US008777877B2

(12) United States Patent
Stein et al.

(10) Patent No.: US 8,777,877 B2
(45) Date of Patent: Jul. 15, 2014

(54) SPINE TOOL FOR MEASURING VERTEBRAL LOAD AND POSITION OF LOAD

(75) Inventors: Marc Stein, Chandler, AZ (US); Andrew Chase, Chandler, AZ (US)

(73) Assignee: Orthosensor Inc., Dania Beach, FL (US)

( * ) Notice: Subject to any disclaimer, the term of this patent is extended or adjusted under 35 U.S.C. 154(b) by 0 days.

(21) Appl. No.: 13/242,278

(22) Filed: Sep. 23, 2011

(65) Prior Publication Data

US 2013/0079790 A1 Mar. 28, 2013

(51) Int. Cl.
| A61B 5/103 | (2006.01) |
| A61B 5/117 | (2006.01) |
| A61B 17/56 | (2006.01) |
| A61F 5/04 | (2006.01) |
| A61B 17/58 | (2006.01) |
| A61B 17/60 | (2006.01) |
| A61F 2/00 | (2006.01) |
| A61B 17/70 | (2006.01) |
| A61B 17/88 | (2006.01) |

(52) U.S. Cl.
USPC .............. 600/594; 600/587; 606/53; 606/102; 606/246; 606/279

(58) Field of Classification Search
USPC .............. 600/587, 594, 595; 606/53, 60, 102, 606/246, 267, 279, 281, 86 A, 86 B
See application file for complete search history.

(56) References Cited

U.S. PATENT DOCUMENTS

| 4,066,082 A | 1/1978 | Arcan et al. |
| 4,899,761 A | 2/1990 | Brown et al. |
| 5,456,724 A | 10/1995 | Yen et al. |
| 5,470,354 A | 11/1995 | Hershberger et al. |
| 6,425,920 B1 * | 7/2002 | Hamada ...................... 623/17.16 |
| 6,739,068 B1 | 5/2004 | Rinner |
| 6,796,988 B2 | 9/2004 | Estes et al. |
| 7,153,281 B2 | 12/2006 | Holmes |
| 7,283,867 B2 | 10/2007 | Strother et al. |
| 7,442,196 B2 | 10/2008 | Fisher et al. |
| 7,819,826 B2 | 10/2010 | Diederich et al. |
| 8,057,482 B2 * | 11/2011 | Stone et al. .................... 606/102 |
| 8,167,823 B2 * | 5/2012 | Nycz et al. ..................... 600/587 |
| 8,211,041 B2 * | 7/2012 | Fisher et al. ................... 600/595 |
| 2002/0049394 A1 | 4/2002 | Roy et al. |
| 2003/0036764 A1 | 2/2003 | Hamada |

(Continued)

FOREIGN PATENT DOCUMENTS

| EP | 1800097 B1 | 6/2007 |
| WO | 2006098759 A1 | 9/2006 |
| WO | 2008120215 A1 | 10/2008 |

*Primary Examiner* — Sean Dougherty
*Assistant Examiner* — Devin Henson

(57) ABSTRACT

A spine measurement system includes at least one spinal instrument and a remote system. The spinal instrument comprises a handle, a shaft, an accelerometer, a sensored head, and an electronic assembly. The sensored head includes one or more sensors that are operatively coupled to the electronic assembly. The sensored head can be inserted between vertebra and report vertebral conditions such as force, pressure, orientation and edge loading. A GUI of remote system can report position via the accelerometer to show spinal instrument relative to vertebral bodies as the instrument is placed in the inter-vertebral space. The system can report optimal prosthetic size and placement in view of the sensed load and location parameters including optional orientation, rotation and insertion angle along a determined insert trajectory.

15 Claims, 16 Drawing Sheets

(56) References Cited

U.S. PATENT DOCUMENTS

| | | |
|---|---|---|
| 2003/0187351 A1 | 10/2003 | Franck et al. |
| 2004/0152970 A1 | 8/2004 | Hunter et al. |
| 2005/0010299 A1 | 1/2005 | Disilvestro |
| 2005/0010302 A1 | 1/2005 | Dietz et al. |
| 2005/0234555 A1 | 10/2005 | Sutton |
| 2006/0069436 A1* | 3/2006 | Sutton et al. ............... 623/17.13 |
| 2007/0129776 A1 | 6/2007 | Robins et al. |
| 2007/0239165 A1* | 10/2007 | Amirouche ................... 606/86 |
| 2007/0276370 A1* | 11/2007 | Altarac et al. ................. 606/61 |
| 2008/0082118 A1 | 4/2008 | Edidin et al. |
| 2008/0133016 A1* | 6/2008 | Heinz ....................... 623/17.16 |
| 2008/0228195 A1 | 9/2008 | Von Jako et al. |
| 2010/0010494 A1 | 1/2010 | Quirno |
| 2010/0022874 A1 | 1/2010 | Wang et al. |
| 2010/0100130 A1 | 4/2010 | Carl et al. |
| 2010/0331633 A1 | 12/2010 | Stein |
| 2010/0331737 A1 | 12/2010 | Stein et al. |
| 2011/0160572 A1 | 6/2011 | McIntosh et al. |
| 2011/0160738 A1 | 6/2011 | McIntosh et al. |

* cited by examiner

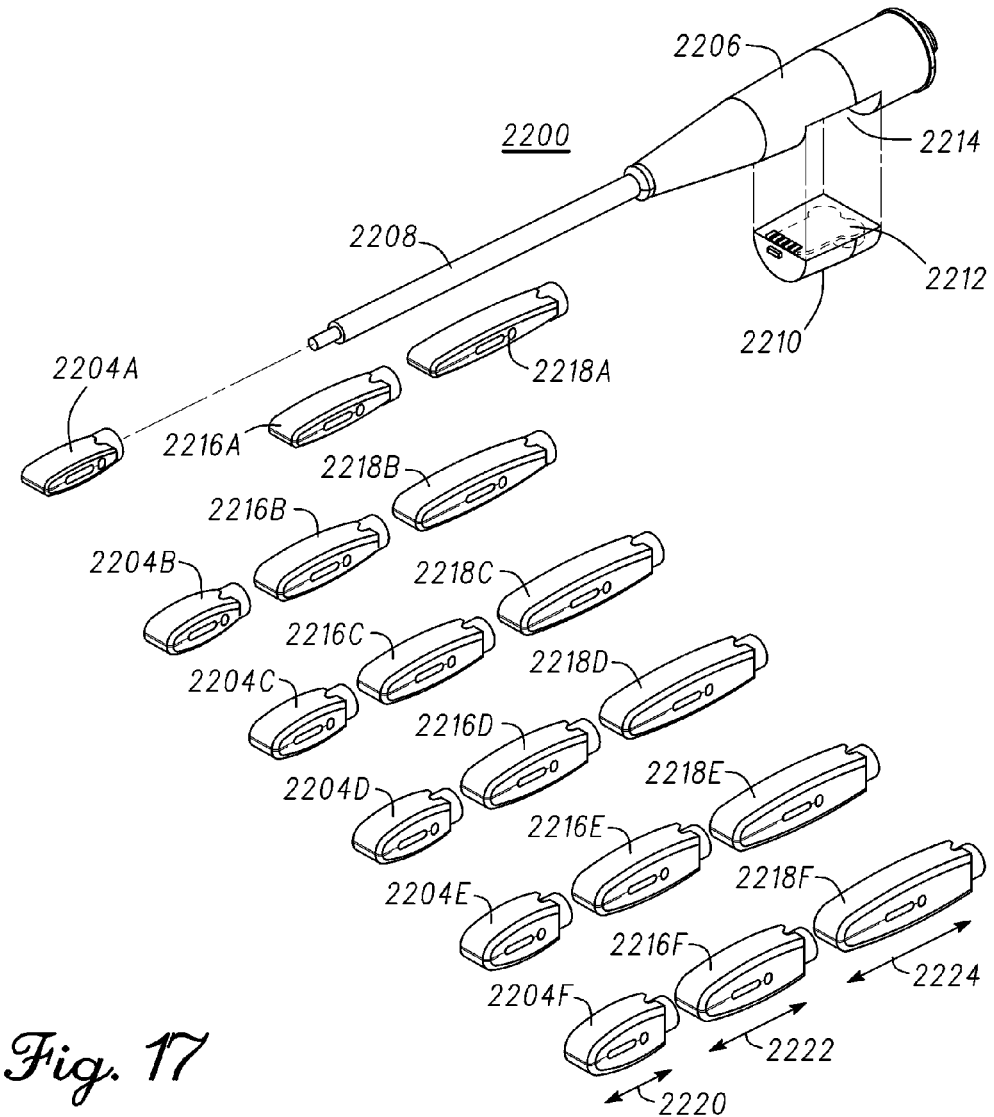
Fig. 17
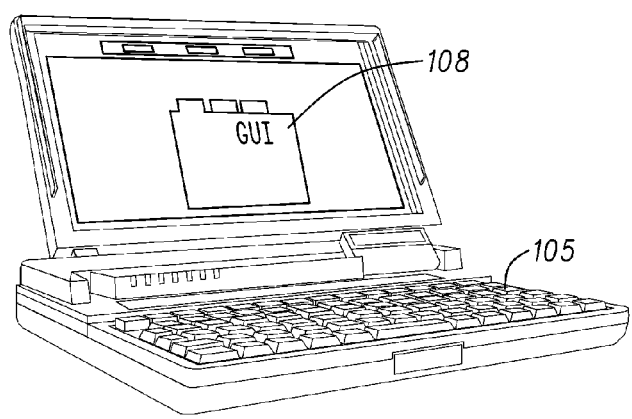

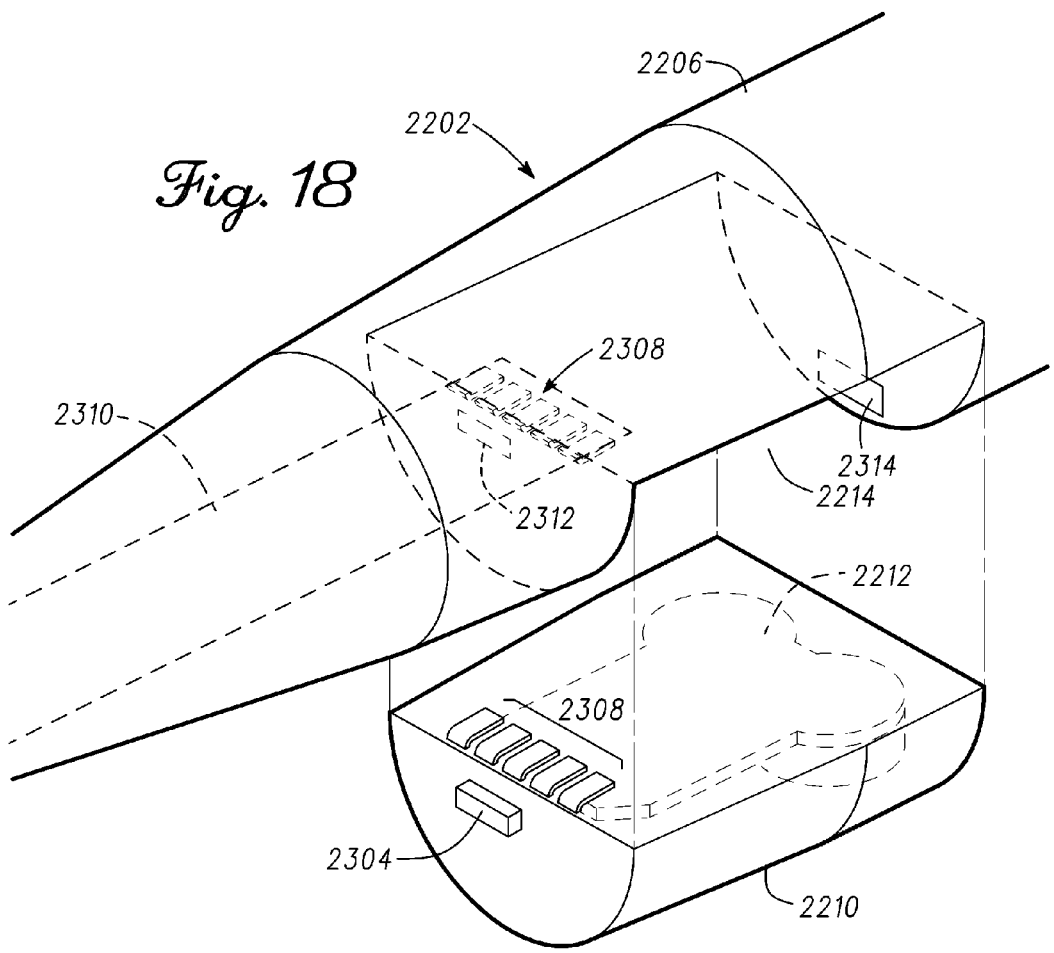
Fig. 18
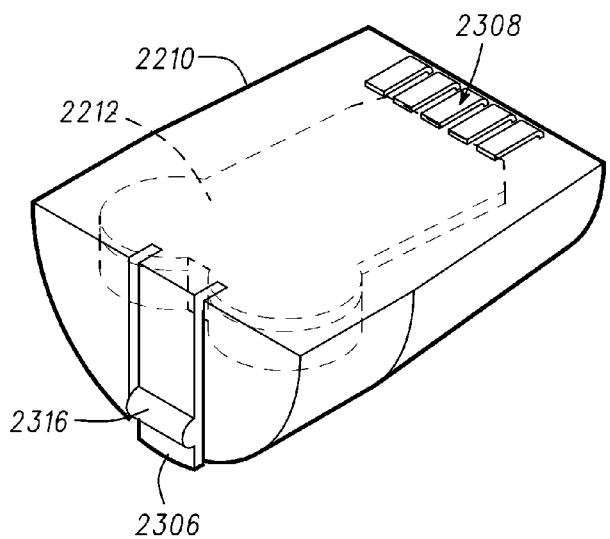

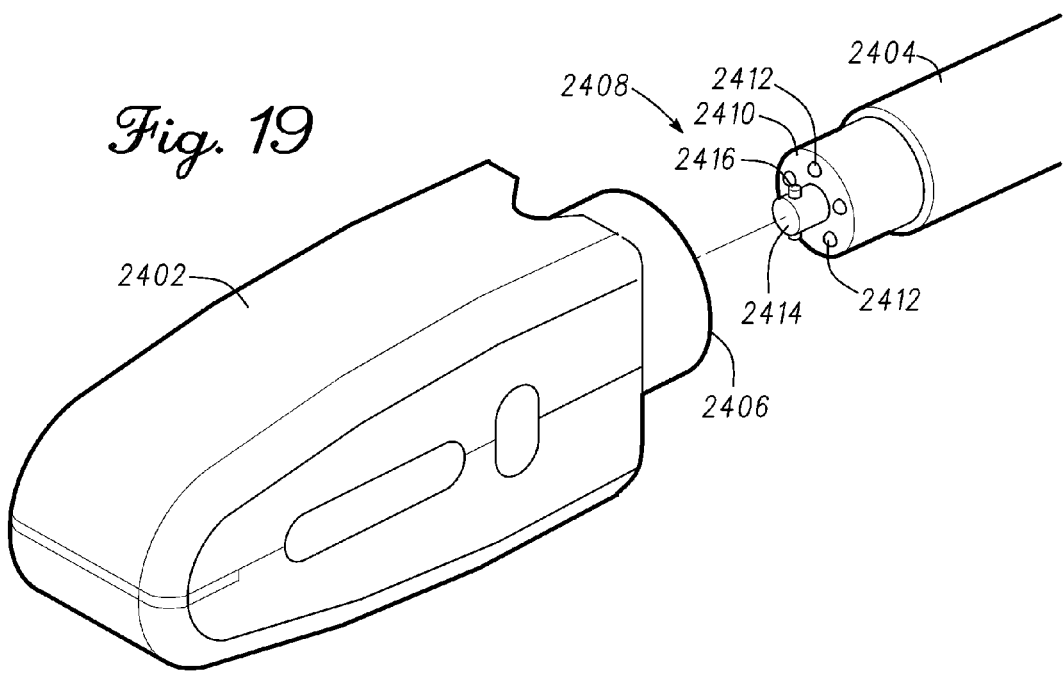
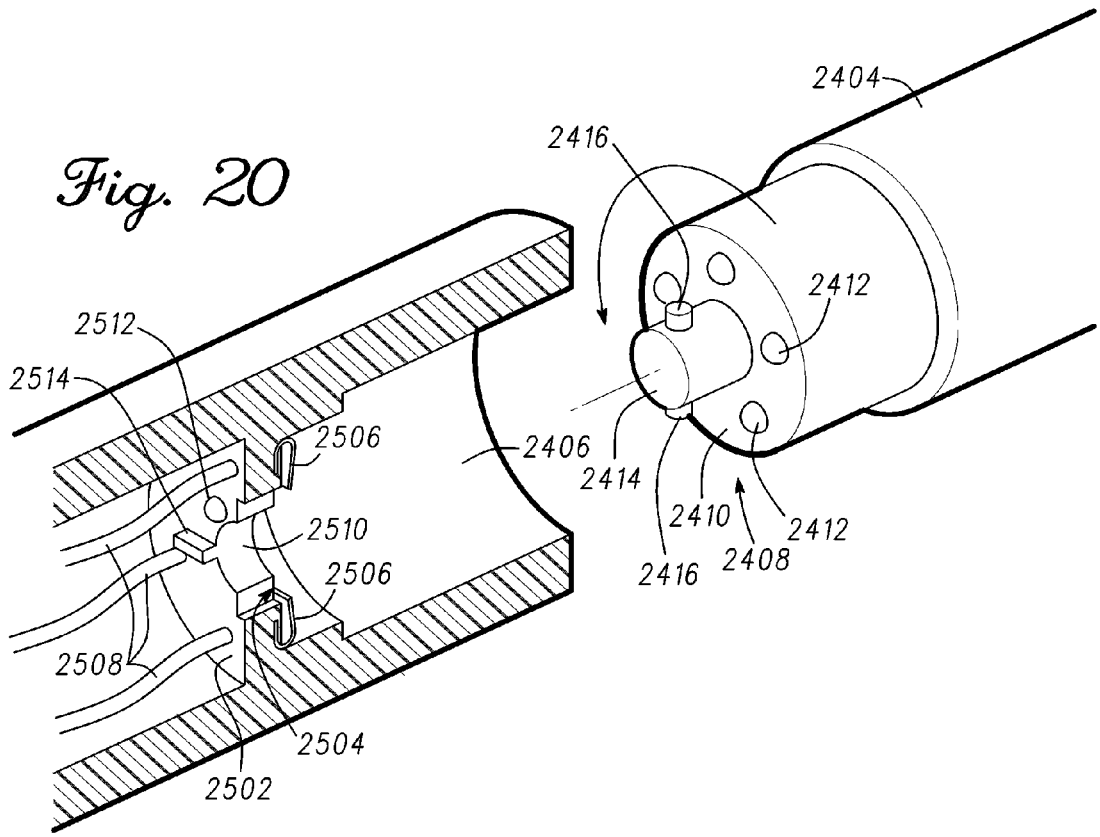

SPINE TOOL FOR MEASURING VERTEBRAL LOAD AND POSITION OF LOAD

FIELD

The present invention pertains generally to surgical electronics, and particularly to methods and devices for assessing alignment and surgical implant parameters during spine surgery and long-term implantation.

BACKGROUND

The spine is made up of many individual bones called vertebrae, joined together by muscles and ligaments. Soft intervertebral discs separate and cushion each vertebra from the next. Because the vertebrae are separate, the spine is flexible and able to bend. The vertebrae provide a conduit for the spinal cord neural bundle. Together the vertebrae, discs, nerves, muscles, and ligaments make up the vertebral column or spine. The spine varies in size and shape, with changes that can occur due to environmental factors, health, and aging. The healthy spine has front-to-back curves, but deformities from normal cervical lordosis, thoracic kyphosis, and lumbar lordosis conditions can cause pain, discomfort, and difficulty with movement. These conditions can be exacerbated by herniated discs, which can pinch nerves.

There are many different causes of abnormal spinal curves and various treatment options from therapy to surgery. The goal of the surgery is a usually a solid fusion of two or more vertebrae in the curved part of the spine. A fusion is achieved by operating on the spine and adding bone graft. The vertebral bones and bone graft heal together to form a solid mass of bone called a fusion. Alternatively, a spinal cage is commonly used that includes bone graft for spacing and fusing vertebrae together. The bone graft may come from a bone bank or the patient's own hipbone or other autologous site. The spine can be substantially straightened with metal rods and hooks, wires or screws via instrumented tools and techniques. The rods or sometimes a brace or cast hold the spine in place until the fusion has a chance to heal.

BRIEF DESCRIPTION OF THE DRAWINGS

Various features of the system are set forth with particularity in the appended claims. The embodiments herein, can be understood by reference to the following description, taken in conjunction with the accompanying drawings, in which:

FIG. 17 illustrates a spine measurement system for providing intervertebral load and position of load data in accordance with an example embodiment;

FIG. 18 illustrates an exploded view of the module and the handle in accordance with an example embodiment;

FIG. 19 illustrates a shaft for receiving a removable sensored head in accordance with an example embodiment;

FIG. 20 illustrates a cross-sectional view of a female coupling of the sensored head in accordance with an example embodiment;

DETAILED DESCRIPTION

Figure 1:
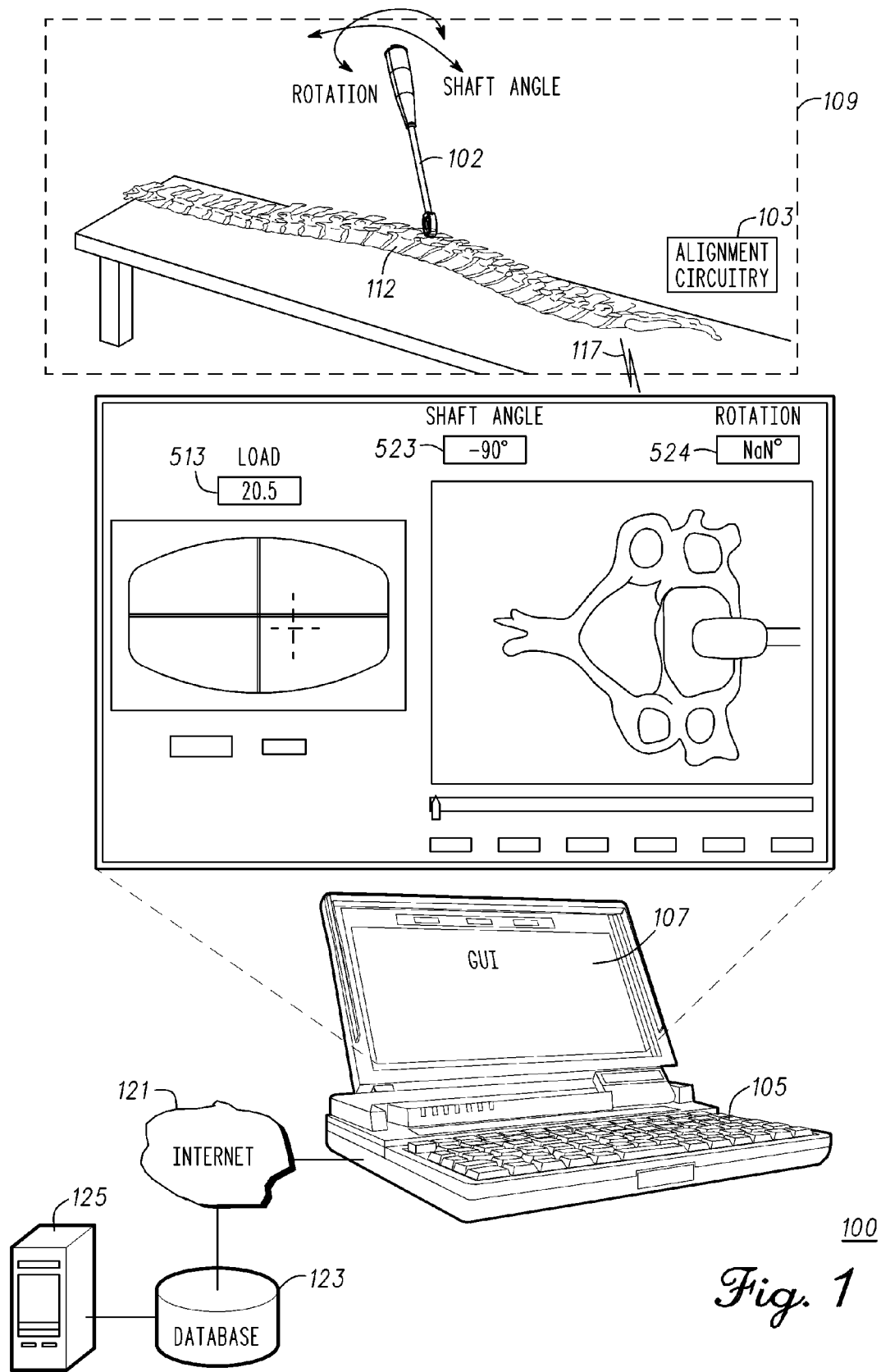
FIG. 1 illustrates a spine measurement system in accordance with an example embodiment.

While the specification concludes with claims defining the features of the embodiments of the invention that are regarded as novel, it is believed that the method, system, and other embodiments will be better understood from a consideration of the following description in conjunction with the drawing figures, in which like reference numerals are carried forward.

As required, detailed embodiments of the present method and system are disclosed herein. However, it is to be understood that the disclosed embodiments are merely exemplary, which can be embodied in various forms. Therefore, specific structural and functional details disclosed herein are not to be interpreted as limiting, but merely as a basis for the claims and as a representative basis for teaching one skilled in the art to variously employ the embodiments of the present invention in virtually any appropriately detailed structure. Further, the terms and phrases used herein are not intended to be limiting but rather to provide an understandable description of the embodiment herein.

Broadly stated, embodiments of the invention are directed to a system and method for vertebral load and location sensing. A spine measurement system comprises a spinal instrument coupled to a remote display. The spine measurement system can measure load, balance, and alignment to assess load forces on the vertebra. The spinal instrument can be an active device having an electronic assembly and a sensorized head assembly that can articulate within a vertebral space. The sensorized head can be inserted between vertebra and report vertebral conditions such as force, pressure, orientation and edge loading. The spine measurement system further includes alignment circuitry. The alignment circuitry provides positional information for identifying an orientation and location of the spinal instrument. A GUI of the remote system can be used to show where the spine instrument is positioned relative to vertebral bodies as the instrument is placed in the inter-vertebral space during the surgical procedure. The system can report optimal prosthetic size and placement in view of the sensed load and location parameters including optional orientation, rotation and insertion angle along a determined insert trajectory.

An insert instrument is also provided herein with the load balance and alignment system for inserting a vertebral component such as a spine cage or pedicle screw. The system in view of previously captured parameter measurements can check and report if the instrument is edge loading during an insertion. It shows tracking of the insert instrument with the vertebral component and provides visual guidance and feedback based on positional and load sensing parameters. The system shows three-dimensional (3D) tracking of the insert instrument in relation to one or more vertebral bodies whose orientation and position are also modeled in 3D.

FIG. 1 illustrates a spine measurement system 100 in a non-limiting example. The system 100 comprises a spinal instrument 102 that can be communicatively coupled to a remote system 105. The spine measurement system 100 can further include alignment circuitry 103 to determine positional information of at least one of an orientation, rotation, angle, and location. The positional information can relate to a tool, device, equipment, patient, or region of the muscular-skeletal system. In the example, alignment circuitry 103 can be part of spinal instrument 102 or comprise external components. In one embodiment, external components comprising alignment circuitry 103 can couple to spinal instrument 102 or to regions of the spine for determining positional information. In one embodiment, location and position can be determined via one or more accelerometers. Alternatively, location and position can be determined via a time of flight or differential time of flight of a signal. The positional information can include orientation and translation data used to assess an alignment of the spine 112. The positional information can be measured in real-time during the procedure or provided to remote system 105.

In the example, spinal instrument 102 can be used intra-operatively to measure a parameter of the spinal region. Spinal instrument 102 includes at least one sensor for measuring the parameter. Spinal instrument 102 can have more than one sensor for measuring different parameters and providing quantitative data to the surgeon in real-time. In one embodiment, spinal instrument 102 measures load, position of load, and alignment. Spinal instrument 102 is not limited to load and alignment measurement example. Other sensor types for measuring different parameters can be integrated into the device. The quantitative data generated by spinal instrument 102 can be used to determine a location for placing a prosthetic component such as a pedicle screw or a spine cage in the spine. Spinal instrument 102 can be used to distract the spinal region being measured. In general, spinal instrument 102 and alignment circuitry 103 may be used within a sterile field 109 of an operating room. The sterile field 109 can also be called a surgical field where a patient operation is performed. Typically, remote system 105 is outside the sterile field 109 of the operating room. The remote system 105 can be a laptop, mobile workstation, display or other device that presents a Graphical User Interface (GUI) 107. In one embodiment, GUI 107 contains a workflow that shows the spine 112 and reports spinal instrument quantitative measurement data. For example, remote system can receive and display load, load position, and alignment data from spinal instrument 102 and alignment circuitry 103. Alternatively, spinal instrument 102 can have an interface for displaying or indicating the quantitative measurement data. In the example, the spinal instrument 102 is a self-contained device for generating measurement data.

The GUI 107 is presented by way of the remote system 105 and spine measurement system 100. In the example, the GUI 107 may have more than one window to show the quantitative measurement data provided by spinal instrument 102 and alignment circuitry 103. GUI 107 is shown on the display of remote system 105 for providing real-time quantitative data from spinal instrument 107 and alignment circuitry 103. In the example, spinal instrument 102 is being directed to a spinal region. More specifically, spinal instrument 102 is being directed between vertebrae of the spine. Sensors can be placed within a sensored head of spinal instrument 102. The sensored head can be used to distract the vertebrae thereby generating a gap between vertebrae that is the height of the sensored head. Spinal instrument 102 can be wired or wirelessly coupled to remote system 105. In the example, spinal instrument 102 is wirelessly coupled to remote system 105 for transmitting data. That transmitted data can include load, location, and position data. GUI 107 can display alignment data in real-time such as shaft angle and a rotation component corresponding to the direction of spinal instrument 102 in relation to the vertebrae of interest. Furthermore, GUI 107 can provide quantitative measurement data on the load and position of load applied by the vertebrae to the sensored head of spinal instrument 102 after insertion. Thus, measurement system 100 allows the surgeon and medical staff to visualize use of the spinal instrument 102 and the sensed parameters.

The spine measurement system 100 can be communicatively coupled to a database 123 system such as a server 125 to provide three-dimensional (3D) imaging (e.g., soft tissue) and 3D models (e.g., bone) captured prior to, or during, surgery. The 3D imaging and models can be used in conjunction with positional information measured during the procedure to establish relative location and orientation. The server 125 may be local in near vicinity or remotely accessed over the Internet 121. As one example, the server 125 provides 3D spine and vertebra models. A CAT scanner (not shown) can be employed to produce a series of cross-sectional x-ray images of a selected part of the body. A computer operates the scanner, and the resulting picture represents a slice of the body. The server 125 produces a three-dimensional (3D) model from the slices. The server 125 can also provide 3D models generated from Magnetic Resonance Imaging (MRI) scanners (not shown). The server 125 may also support fluoroscopic imaging to provide real-time moving images of the internal structures of a patient with respect to the spine measurement system 100 devices through the use of X-ray source (not shown) and fluorescent screen.

In the example, the sensored head of spinal instrument 102 includes a sensor for measuring load. In one embodiment, the sensored head includes more than one sensor for measuring a location of an applied force, pressure, or load to the surfaces of the sensored head. Measuring the location of the applied force to surfaces of the sensored head of spinal instrument 102 provides information related to the spinal region and the distribution of the force. For example, an application may require an even distribution of force applied over a large area of the surfaces of the sensored head. Conversely, an application may require a peak force applied over a small area of the surface of the sensored head. In either example, spinal instrument 102 can provide measurement data related to force magnitude and location of the applied force whereby the surgeon uses the quantitative data in conjunction with subjective information for assessing the probed spinal region.

Many physical parameters of interest within physical systems or bodies can be measured by evaluating changes in the characteristics of energy waves or pulses. As one example, changes in the transit time or shape of an energy wave or pulse propagating through a changing medium can be measured to determine the forces acting on the medium and causing the changes. The propagation velocity of the energy waves or pulses in the medium can be affected by physical changes in of the medium. The physical parameter or parameters of interest can include, but are not limited to, measurement of load, force, pressure, displacement, density, viscosity, and localized temperature. These parameters can be evaluated by measuring changes in the propagation time of energy pulses or waves relative to orientation, alignment, direction, or position as well as movement, rotation, or acceleration along an axis or combination of axes by wireless sensing modules or devices positioned on or within a body, instrument, equipment, or other mechanical system. Alternatively, measurements of interest can be taken using film sensors, mechanical sensors, polymer sensors, mems devices, strain gauge, piezoresistive structure, and capacitive structures to name but a few.

Figure 2:
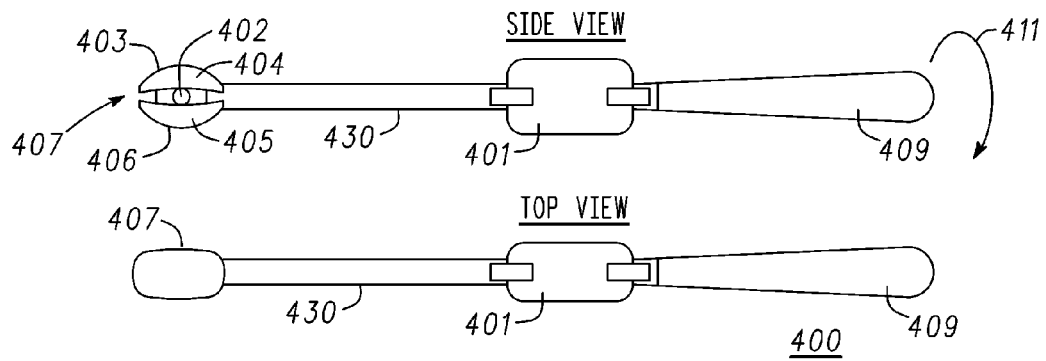
FIG. 2 illustrates a spinal instrument in a non-limiting example.

FIG. 2 illustrates a spinal instrument 400 in a non-limiting example. A side view and a top view are presented. Spinal instrument 400 is a more detailed illustration of a non-limiting example of spinal instrument 102 of FIG. 1. Spinal instrument 400 comprises a handle 409, a shaft 430, and a sensored head 407. The handle 409 is coupled at a proximal end of the shaft 430. Sensored head 407 is coupled to a distal end of the shaft 430. A surgeon holds spinal instrument 400 by the handle 409 to direct shaft 430 and sensored head 407 to a spinal region. In one embodiment, handle 409, shaft 430, and sensored head 407 form a rigid structure that has little flex. Alternatively, one or more of handle 409, shaft 430, and sensored head 407 may have some flexibility. Spinal instrument 400 includes an electronic assembly 401 operatively coupled to one or more sensors. The sensors can be coupled to surfaces 403/406 on moving components 404/405 of sensored head 407. Electronic assembly 401 can be located towards the proximal end of the shaft 407 or in handle 409. As shown, the electronic assembly 401 is a module that is coupled to shaft 409. Electronic assembly 401 comprises electronic circuitry that includes logic circuitry, an accelerometer, and communication circuitry. The electronic circuitry controls sensor measurement, receives measurement data, stores the data, and can send the data to an external device.

In one embodiment, surfaces 403 and 406 of sensored head 407 can have a convex shape. The convex shape of surfaces 403 and 406 support placement of sensored head 407 within the spinal region and more specifically between the contours of vertebrae. In one embodiment, sensored head 407 is height adjustable by way of the top component 404 and the bottom component 405 through a jack 402 that evenly distracts and closes according to handle 409 turning motion 411. Jack 402 is coupled to interior surfaces of components 404 and 405 of sensored head 407. Shaft 430 includes one or more lengthwise passages. For example, interconnect such as a flexible wire interconnect can couple through one lengthwise passage of shaft 430 such that electronic assembly 401 is operatively coupled to one or more sensors in sensored head 407. Similarly, a threaded rod can couple through a second passage of shaft 430 for coupling handle 409 to jack 404 thereby allowing height adjustment of sensored head 407 via rotation of handle 409.

Spine instrument 400 can also determine location and orientation by way of one or more embedded accelerometers. The sensored head 407 supports multiple functions that include the ability to determine a parameter of the procedure area (e.g., intervertebral space) including pressure, tension, shear, load, torque, bone density, and/or bearing weight. In one embodiment, more than one load sensor can be included within sensored head 407. The more than one load sensors can be coupled to predetermined locations of surfaces 403 and 406. Having more than one load sensor allows the sensored head 407 to measure load magnitude and the position of applied load to surfaces 403 and 406. The sensored head 407 can be used to measure, adjust, and test a vertebral joint prior to installing a vertebral component. As will be seen ahead, measurement system 100 can evaluate the optimal insertion angle and position of spinal instrument 400 during intervertebral load sensing. The measurement system 100 can replicate insertion angle and position for instrument 400 or for another tool such as an insertion instrument.

In the present invention these parameters can be measured with an integrated wireless sensored head 407 or device comprising an i) encapsulating structure that supports sensors and contacting surfaces and ii) an electronic assemblage that integrates a power supply, sensing elements, ultrasound resonator or resonators or transducer or transducers and ultrasound waveguide or waveguides, biasing spring or springs or other form of elastic members, an accelerometer, antennas and electronic circuitry that processes measurement data as well as controls all operations of energy conversion, propagation, and detection and wireless communications. Sensored head 407 or instrument 400 can be positioned on or within, or engaged with, or attached or affixed to or within, a wide range of physical systems including, but not limited to instruments, appliances, vehicles, equipments, or other physical systems as well as animal and human bodies, for sensing and communicating parameters of interest in real time.

Spinal instrument 400 can be used in the installation of a spinal cage as a non-limiting example. The spinal cage is used to space vertebrae in replacement of a disc. The spinal cage is typically hollow and can be formed having external threads for fixation. Two or more cages are often installed between the vertebrae to provide sufficient support and distribution of loading over the range of motion. In one embodiment, the spinal cage may be made of titanium for supporting spinal load and spacing between vertebrae. A bone growth material can also be placed in the cage to initiate and promote bone growth thereby further strengthening the intervertebral area long-term. Spinal instrument 400 can be used to provide quantitative data such as load and position of load for a region between vertebrae that may be a candidate for a prosthetic component such as the spinal cage. Typically, spinal instrument 400 is inserted in a gap selected by the surgeon between vertebrae. Spinal instrument 400 measures load and position of load that can be viewed on an interface on the device or to a remote system such as that disclosed in FIG. 1. The position of load corresponds to the vertebral area surfaces applying the load on surfaces 403 or 406 of sensored head 407. The angle and position of insertion of the sensed head 407 of spinal instrument 400 can also be measured. The load magnitude and position of load measurement are used by the surgeon to determine an implant location between the vertebrae and the size of the spinal cage for the implant location. Typically, the height and length of the selected spinal cage is approximately the height and length of sensed head 407. Moreover, the area chosen for the spinal cage location may load the prosthetic component within a predetermined load range as measured by spinal instrument 400. Conversely, quantitative measurements of vertebral loading outside the predetermined range may be found unsuitable for prosthetic component installation. The surgeon can modify the contact surfaces of the vertebrae to fall within the predetermined range as measured by spinal instrument 400. The surgeon can also locate a different region between the vertebrae that is more suitable based on quantitative data provided by spinal instrument 400.

In the example, a spinal cage is inserted in the measured region after removing the sensed head 407. The spinal cage can be inserted in the same location measured by sensed head 407 using quantitative measurement data. The alignment data of spinal instrument 400 is generated and recorded during an insertion process and measurement of load and position of load. The loading on the implanted spinal cage when inserted in the same position and angle as sensed head 407 is approximately equal to the measurements made by spinal instrument 400. The recorded angle and position measurements can be subsequently used to guide the spinal cage into the same location and more specifically by a similar insertion path as spinal instrument 400. In one embodiment, spinal instrument 400 can be used to place the prosthetic component into the identified region. A separate instrument can also be used for insertion of the prosthetic component.

Figure 3:
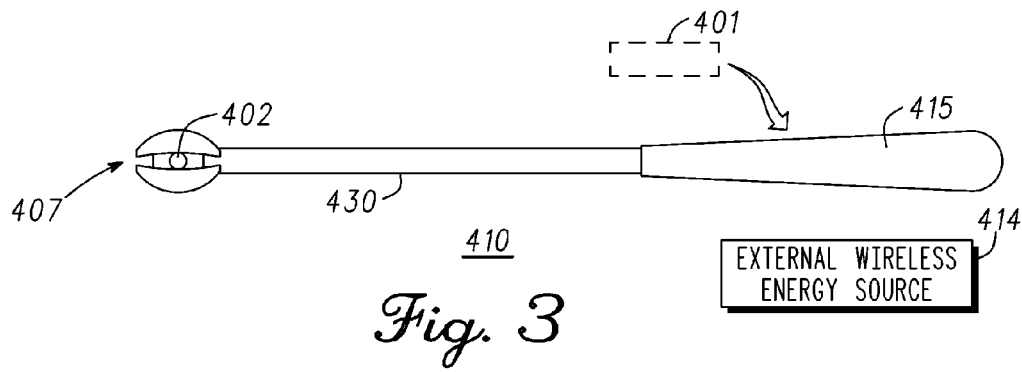
FIG. 3 illustrates a spinal instrument having integrated electronics in a non-limiting example.

FIG. 3 illustrates a spinal instrument 410 having integrated electronics in a non-limiting example. Spinal instrument 410 is a more detailed illustration of a non-limiting example of spinal instrument 102 of FIG. 1 and relates to spinal instrument 400. Electronic assembly 401 is placed within handle 415 of spinal instrument 410. Placing electronic assembly 401 in handle 415 provides the benefit of isolating the circuitry from the external environment. Handle 415 can further provide shock isolation for the electronic assembly 401 for reliability. In one embodiment, an external wireless energy source 414 can be placed in proximity to a charging unit within electronic assembly 401 to initiate a wireless power recharging operation. The wireless energy source 414 can include a power supply, a modulation circuit, and a data input. The power supply in energy source 414 can be a battery, a charging device, a capacitor, a power connection, or other energy source for generating wireless power signals that can transfer power to spinal instrument 410. The external wireless energy source 414 can transmit energy in the form of, but not limited to, electromagnetic induction, or other electromagnetic or ultrasound emissions. In at least one exemplary embodiment, the wireless energy source includes a coil to electromagnetically couple and activate (e.g., power on) with an induction coil in sensing device when placed in close proximity.

Electronic assembly 401 operatively couples to sensors in sensed head 407 for measuring a parameter. Electronic assembly 401 includes communication circuitry for transmitting measured parameter data to a receiver via data communications circuitry. The received parameter data can be processed remotely to permit visualization of the level and distribution of the parameter at various points on the sensed head. Information can also be provided to electronic assembly 401 using external wireless energy source 414. Data can be provided through an interface or port to external wireless energy source 414. The information or data can be input from another data source, such as from a computer via a wired or wireless connection (e.g., USB, IEEE802.16, etc.). In one embodiment, external wireless energy source 414 includes a modulation circuitry that can modulate the input information onto the power signals for sourcing energy to electronic assembly 401. In the example, electronic assembly 401 has demodulation circuitry coupled for removing and providing the information for use by spinal instrument 410 from the power signals.

Figure 4:
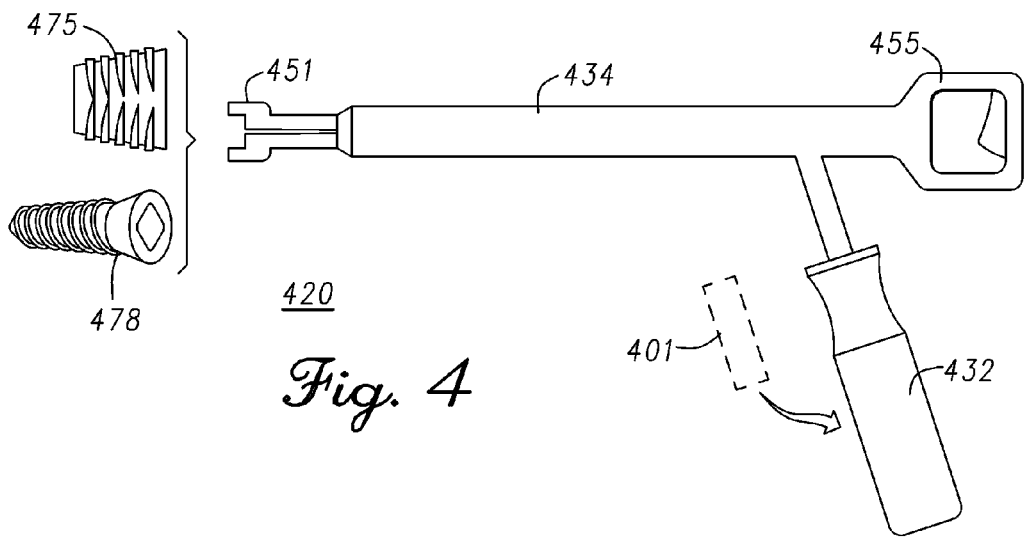
FIG. 4 illustrates an insert instrument with vertebral components in a non-limiting example.
Figure 11:
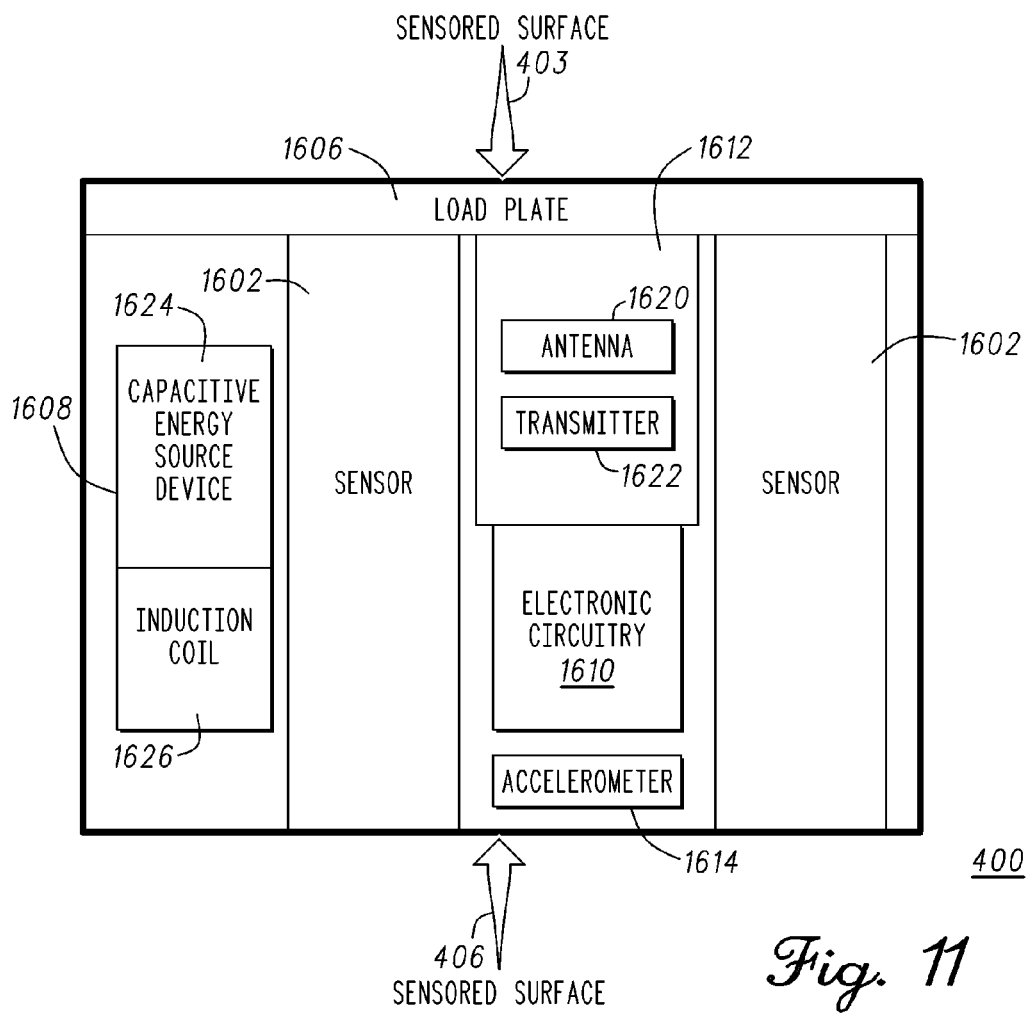
FIG. 11 is a block diagram of the components of the spinal instrument in accordance with an example embodiment.
Figure 12:
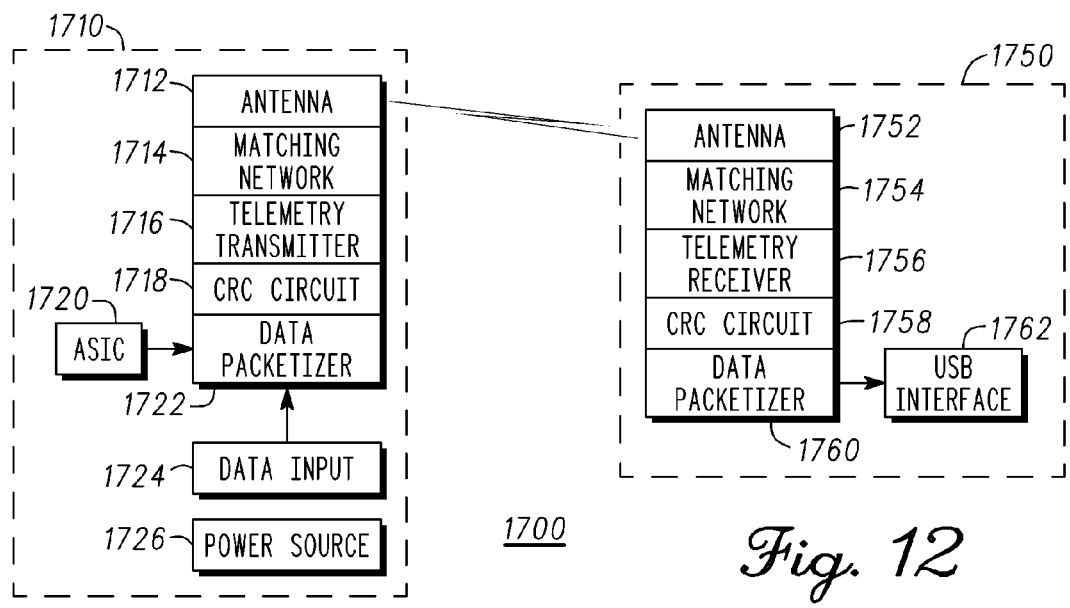
FIG. 12 is a diagram of an exemplary communications system for short-range telemetry in accordance with an example embodiment.

FIG. 4 illustrates an insert instrument 420 with vertebral components in a non-limiting example. Electronic assembly 401 as described herein supports the generation of orientation and position data of insert instrument 420. In one embodiment, electronic assembly 401 includes an accelerometer for providing orientation and position data. Referring to FIG. 11 briefly, electronic assembly 401 of insert instrument 420 can have more or less circuitry than that disclosed for spinal instruments 400 and 410. By way of measurement system 100, the user can replicate the insertion angle, position and trajectory (path) to achieve proper or pre-planned placement of a vertebral component. Insert instrument 420 comprises a handle 432, a shaft 434, and a tip 451. An attach/release mechanism 455 couples to the proximal end of shaft 434 for controlling tip 451. Attach/release mechanism 455 allows a surgeon to retain or release vertebral components coupled to tip 451. Attach/release mechanism 455 can mechanically couple through shaft 434 to control tip 451. Alternatively, attach/release mechanism 455 can be an electronic control. In the example, handle 432 extends at an angle in proximity to a proximal end of shaft 434. Positioning of handle 432 allows the surgeon to accurately direct tip 451 in a spinal region while allowing access to attach/release mechanism 455. Electronic assembly can be housed in handle 432 or attached to insert instrument 420. Referring to FIG. 12 briefly, electronic assembly 401 includes communication circuitry to securely transmit and receive data from a remote system. Insert instrument 420 is a tool of spine measurement system 100. Quantitative measurement data such as orientation and position data can be transmitted to remote system 105 of FIG. 1 for real time and visualization of an insertion process. Electronic assembly 401 can also couple to one or more sensors of insert instrument 420. In a first example, tip 451 can be coupled to a pressure sensor to determine a force, pressure, or load being applied by the spinal region to a prosthetic component coupled thereto. In a second example, tip 451 can be removable such that a sensed head can be coupled to insert instrument 420. In a third example, the prosthetic component can include a sensor. The sensor of the prosthetic component includes an interface that couples to electronic assembly 401 for providing quantitative measurement data.

In the illustration, an example prosthetic component is a spine cage 475. Spine cage 475 is a small hollow device, usually made of titanium, with perforated walls that can be inserted between the vertebrae of the spine during a surgery. In general, a distraction process spaces the vertebrae to a predetermined distance prior insertion of spine cage 475. Spine cage 475 can increase stability, decrease vertebral compression, and reduce nerve impingement as a solution to improve patient comfort. Spine cage 475 can include surface threads that allow the cage to be self-tapping and provide further stability. Spine cage 475 can be porous to include bone graft material that supports bone growth between vertebral bodies through cage 475. More than one spine cage can be placed between vertebrae to alleviate discomfort. Proper placement and positioning of spine cage 475 is important for successful long-term implantation and patient outcome. As mentioned above, the orientation and position of insert instrument 420 can be tracked in real-time in relation to the spinal region of interest. In one embodiment, the orientation and position being tracked is a prosthetic component retained by insert instrument 420. In the example, the prosthetic component is spine cage 475. Spine cage 475 can be tracked in 3D space because the location of the prosthetic component is known in relation to the spinal instrument 420 and the one or more measurement accelerometers therein.

In the illustration a second prosthetic component is a pedicle screw 478. The pedicle screw 478 is a particular type of bone screw designed for implantation into a vertebral pedicle. There are two pedicles per vertebra that couple to other structures (e.g. lamina, vertebral arch). A polyaxial pedicle screw may be made of titanium to resist corrosion and increase component strength. The pedicle screw length ranges from 30 mm to 60 mm. The diameter ranges from 5.0 mm to 8.5 mm. It is not limited to these dimensions, which serve as dimensional examples. Pedicle screw 478 can be used in instrumentation procedures to affix rods and plates to the spine to correct deformity, and/or treat trauma. It can be used to immobilize part of the spine to assist fusion by holding bony structures together. By way of electronic assembly 401 (which may be internally or externally integrated), the insert instrument 420 can determine depth and angle for screw placement and guide the screw therein. In the example, one or more accelerometers are used to provide orientation, rotation, angle, or position information of tip 451 during an insertion process.

In one arrangement, the screw 478 is embedded with sensors. The sensors can transmit energy and obtain a density reading and monitor the change in density over time. As one example, the measurement system 100 can monitor and report healing of a fracture site. The sensors can detect the change in motion at the fracture site as well as the motion between the screw and bone. Such information aids in monitoring healing and gives the healthcare provider an ability to monitor vertebral weight bearing as indicated. The sensors can also be activated externally to send energy waves to the fracture itself to aid in healing.

Figure 5:
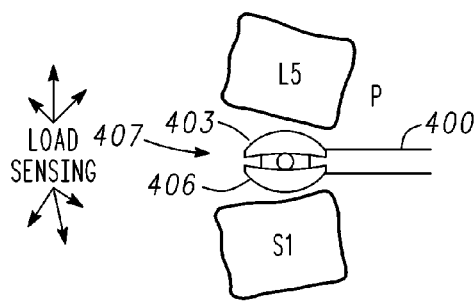
FIG. 5 illustrates a lateral view of the spinal instrument positioned between vertebrae of the spine for sensing vertebral parameters in a non-limiting example.

FIG. 5 illustrates a lateral view of spinal instrument 400 positioned between vertebrae of the spine for sensing vertebral parameters in a non-limiting example. The illustration can also apply to spinal instrument 410 and insert instrument 420. In general, a compressive force is applied to surfaces 403 and 406 when sensored head 407 is inserted into the spinal region. In one embodiment, sensored head 407 includes two or more load sensors that identify magnitude vectors of loading on surface 403, surface 406, or both associated with inter-vertebral force there between. In the example shown, the spinal instrument 400 is positioned between vertebra (L5) and the Sacrum (S1) such that a compressive force is applied to surfaces 403 and 406. One approach for inserting the instrument 400 is from the posterior (back side) through a minilaparotomy as an endoscopic approach may be difficult to visualize or provide good exposure. Another approach is from the anterior (front side) which allows the surgeon to work through the abdomen to reach the spine. In this way spine muscles located in the back are not damaged or cut; avoiding muscle weakness and scarring. Spinal instrument 400 can be used with either the anterior or posterior spine approach.

Aspects of the sensorized components of the spine instrument 400 are disclosed in U.S. patent application Ser. No. 12/825,638 entitled "System and Method for Orthopedic Load Sensing Insert Device" filed Jun. 29, 2010, and U.S. patent application Ser. No. 12/825,724 entitled "Wireless Sensing Module for Sensing a Parameter of the Muscular-Skeletal System" filed Jun. 29, 2010 the entire contents of which are hereby incorporated by reference. Briefly, the sensored head 407 can measure forces (Fx, Fy, and Fz) with corresponding locations and torques (e.g. Tx, Ty, and Tz) and edge loading of vertebrae. The electronic circuitry 401 (not shown) controls operation and measurements of the sensors in sensored head 407. The electronic circuitry 401 further includes communication circuitry for short-range data transmission. It can then transmit the measured data to the remote system to provide real-time visualization for assisting the surgeon in identifying any adjustments needed to achieve optimal joint balancing.

A method of installing a component in the muscular-skeletal system is disclosed below. The steps of the method can be performed in any order. An example of placing a cage between vertebrae is used to demonstrate the method but the method is applicable to other muscular-skeletal regions such as the knee, hip, ankle, spine, shoulder, hand, arm, and foot. In a first step, a sensored head of a predetermined width is placed in a region of the muscular-skeletal system. In the example, the insertion region is between vertebrae of the spine. A hammer can be used to tap an end of the handle to provide sufficient force to insert the sensored head between the vertebrae. The insertion process can also distract the vertebrae thereby increasing a separation distance. In a second step, the position of the load applied to the sensored head is measured. Thus, the load magnitude and the position of the loading on the surfaces of the sensored head are available. How the load applied by the muscular-skeletal system is positioned on the surfaces of the sensored head can aid in determining stability of the component once inserted. An irregular loading applied to sensored head can predict a scenario where the applied forces thrust the component away from the inserted position. In general, the sensored head is used to identify a suitable location for insertion of the component based on quantitative data. In a third step, the load and position of load data from the sensored head is displayed on a remote system in real-time. Similarly, in a fourth step, the at least one of orientation, rotation, angle, or position is displayed on the remote system in real-time. Changes made in positioning the sensored head are reflected in data on the remote system display. In a fifth step, a location between vertebrae having appropriate loading and position is identified and the corresponding quantitative measurement data is stored in memory.

In a sixth step, the sensored head is removed. In a seventh step, the component is inserted in the muscular-skeletal system. As an example, the stored quantitative measurement data is used to support the positioning of the component in the muscular-skeletal system. In the example, the insertion instrument can be used to direct the component into the muscular-skeletal system. The insertion instrument is an active device providing orientation, rotation, angle, or position of the component as it is being inserted. The previously measured direction and location of the insertion of the sensored head can be used to guide the insertion instrument. In one embodiment, the remote system display can aid in displaying relational alignment of the insertion instrument and component to the previously inserted sensored head. The insertion instrument in conjunction with the system can provide visual, vocal, haptic or other feedback to further aid in directing the placement of the component. In general, the component being inserted has substantially equal height and length as the sensored head. Ideally, the component is inserted identical in location and position to the previously inserted sensored head such that the loading and position of load on the component is similar to the quantitative measurements. In an eighth step, the component is positioned identically to the previously inserted sensored head and released. The insertion instrument can then be removed from the muscular-skeletal system. In a ninth step, at least the sensored head is disposed of.

Thus, the sensored head is used to identify a suitable location for insertion of the component. The insertion is supported by quantitative measurements that include position and location. Furthermore, the approximate loading and position of loading on the component is known after the procedure has been completed. In general, knowing the load applied by the muscular-skeletal system and the position on the surfaces of the component can aid in determining stability of the component long-term. An irregular loading applied on the component can result in the applied forces thrusting the component away from the inserted position.

Figure 6:
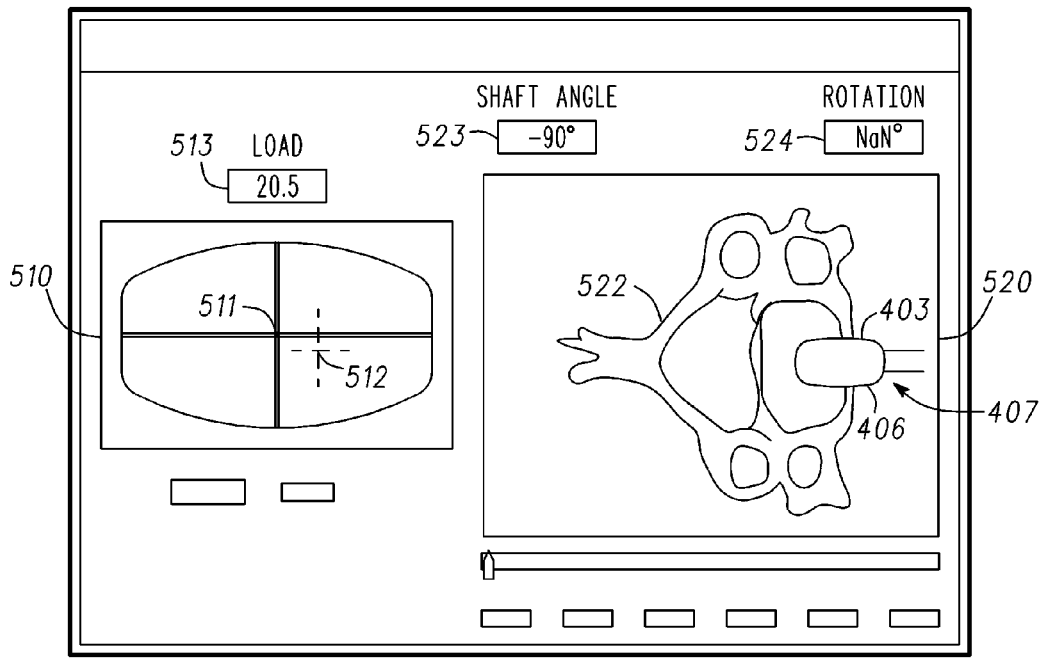
FIG. 6 illustrates a graphical user interface (GUI) showing a axial view of the spinal instrument of FIG. 5 in accordance with an example embodiment.

FIG. 6 illustrates a graphical user interface (GUI) 500 showing a axial (top) view of the sensorized spinal instrument of FIG. 5 in a non-limiting example. The graphical user interface 500 is presented by way of the remote system 105 and spine measurement system 100 of FIG. 1. Reference is made to spinal instrument 400 of FIG. 2 and measurement system 100 of FIG. 1. The GUI 500 illustrates an example of how data can be presented. The GUI 500 includes a window 510 551 and a related window 557. The window 557 shows the spine instrument 400 and sensor head 407 in relation to vertebrae 522 under evaluation. In this example, an axial (top) view of the vertebra is shown. It indicates a shaft angle 523 and a rotation component 524 which reveal the approach angle and rotation of the spine instrument 400, for instance, as it is moved forward into the incision. The window 557 and corresponding GUI information is presented and updated in real-time during the procedure. It permits the surgeon to visualize use of spinal instrument 400 and the sensed parameters. The window 551 shows a sensing surface (403 or 406) of the sensored head 407. A cross hair 553 is superimposed on the sensor head image to identify the maximal point of force and location. It can also lengthen to show vertebral edge loading. A window 555 reports the load force, for example, 20 lbs across the sensor head surface. This information is presented and updated in real-time during the procedure.

As previously noted, spine measurement system 100 can be used intra-operatively to aid in the implantation of the prosthesis, instrumentation, and hardware by way of parameter sensing (e.g., vertebral load, edge loading, compression, etc.). The spinal instrument 400 can include a power source that can provide power for only a single use or procedure. In one embodiment, components such as spinal instrument 400 can be disposed of after being used in a procedure. The remote system 105 can be placed outside the surgical field for use in different procedures and with different tools.

In the spine, the affects on the bony and soft tissue elements are evaluated by the measurement system 100, as well as the soft tissue (e.g., cartilage, tendon, ligament) changes during surgery, including corrective spine surgery. The sensors of a tool, device, or implant used during the operation (and post-operatively) can support the evaluation and visualization of changes over time and report dynamic changes. The sensors can be activated intra-operatively when surgical parameter readings are stored. Immediately post-operatively, the sensor is activated and a baseline is known.

The measurement system 100 allows evaluation of the spine and connective tissue regarding, but not limited to bone density, fluid viscosity, temperature, strain, pressure, angular deformity, vibration, load, torque, distance, tilt, shape, elasticity, and motion. Because the sensors span a vertebral space, they can predict changes in the vertebral component function prior to their insertion. As previously noted, the measurement system 100 can be used to place spine instrument 400 in the inter-vertebral space, where it is shown positioned relative to the vertebral body 522. Once it is placed and visually confirmed in the vertebral center, the system 100 reports any edge loading on the instrument which in turn is used to size a proper vertebral device and insertion plan (e.g., approach angle, rotation, depth, path trajectory). Examples of implant component function include bearing wear, subsidence, bone integration, normal and abnormal motion, heat, change in viscosity, particulate matter, kinematics, to name a few.

Figure 7:
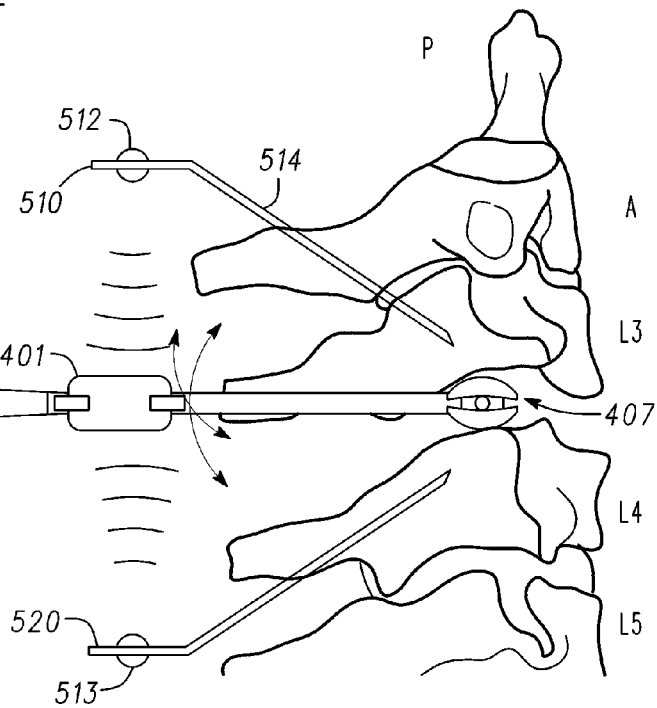
FIG. 7 illustrates the spinal instrument positioned between vertebra of the spine for intervertebral position and force sensing in accordance with an example embodiment.

FIG. 7 illustrates spinal instrument 400 positioned between vertebra of the spine for intervertebral position and force sensing in accordance with an example embodiment. Reference is made to spinal instrument 400 of FIG. 2 and measurement system 100 of FIG. 1. The illustration can also apply to spinal instrument 410 of FIG. 3 and insert instrument 420 of FIG. 4. As shown, sensored head 407 of spinal instrument 400 is placed between vertebrae L3 and vertebrae L4. The spinal instrument 400 distracts the L3 and L4 vertebrae the height of sensored head 407 and provides quantitative data on load magnitude and position of load. As mentioned previously, the spine measurement system 100 can include alignment circuitry 103. The alignment circuitry 103 can comprise external devices such as a wand 510 and a wand 520. Wands 510 and 520 can include accelerometers or circuitry to generate signals for time of flight and differential time of flight measurements. Wands 510 and 520 are coupled to different areas of the spinal region. In one embodiment, spinal instrument 400 includes circuitry that communicates with wand 510 and a wand 520 to determine position and alignment. Wands 510 and 520 are coupled to different vertebra of the spine with spinal instrument 400 positioned to be in line of sight with each wand. A long shaft 514 is provided on each wand to permit placement within vertebra of the spine and also line up with other wands and an electronic assembly 401 of the spine instrument 400. Wand 510 tracks an orientation and position of vertebra L3, while wand 520 tracks an orientation and position of vertebra L4. This permits the spine measurement system 100 to track an orientation and movement of the spine instrument 400 relative to movement of the neighboring vertebra. Each wand can also be sensorized similar to spinal instrument 400. Wands 510 and wand 520 respectively includes a sensor 512 and a sensor 513. Sensors 512 and 513 can transmit and receive positional information. In the example, electronic assembly 401 in conjunction with wands 510 and 520 dually serves to resolve an orientation and position of spinal instrument 400 during the procedure. Thus, spine measurement system 100 can simultaneously provide quantitative measurement data such as load and position of load, position and alignment of spinal instrument 400, and position and alignment of one or more regions of the spine.

Figure 8:
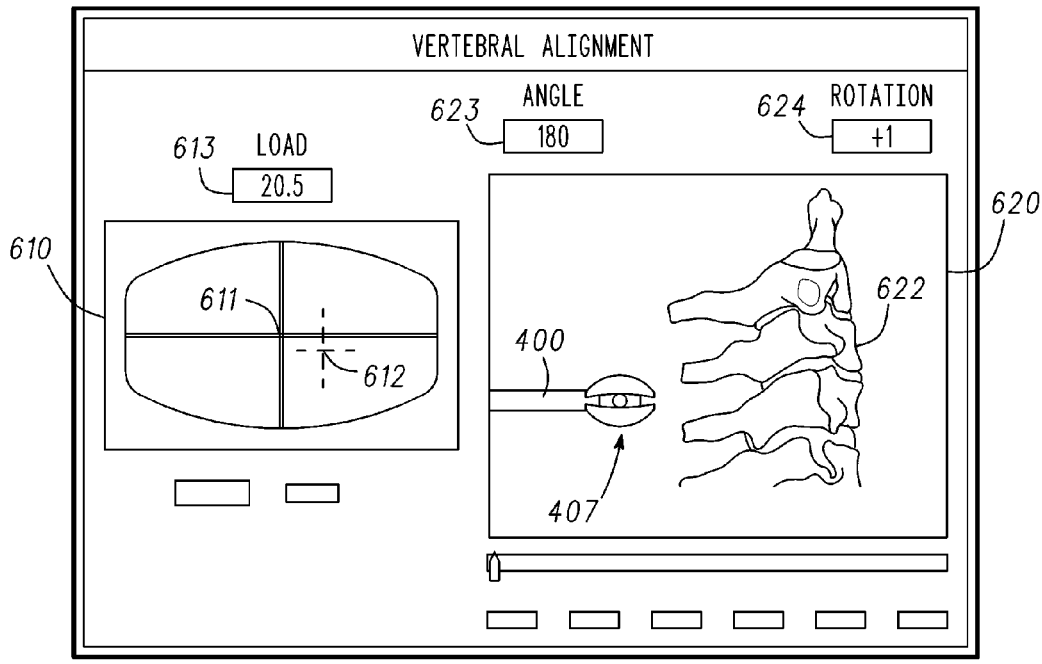
FIG. 8 illustrates a user interface showing the spinal instrument of FIG. 7 in accordance with an example embodiment.

FIG. 8 illustrates user interface 600 showing the spinal instrument 400 of FIG. 7 in accordance with an example embodiment. Reference is made to spinal instrument 400 of FIG. 2 and measurement system 100 of FIG. 1. The illustration can also apply to spinal instrument 410 of FIG. 3 and insert instrument 420 of FIG. 4. User interface 600 is presented by way of the remote system 105 and spine measurement system 100 (see FIG. 1). The GUI 600 includes a window 610 and a related window 620. The window 620 shows spinal instrument 400 and sensored head 407 in relation to a vertebral component 622 under evaluation. In this example, a sagital view of the spine column is shown. It indicates a shaft angle 623 and a rotation component 624 which reveal the approach angle and rotation of spinal instrument 400 and sensored head 407. The window 620 and corresponding GUI information is presented and updated in real-time during the procedure. It permits the surgeon to visualize sensed head 407 of the spinal instrument 400 and the sensed load force parameters. The window 610 shows sensing surfaces of the sensor head 407. A cross hair 612 is superimposed on the image of sensed head 407 to identify the maximal point of force and location. It can also adjust in width and length to show vertebral edge loading. Another GUI window 613 reports the load force across the sensored head 407 surface. The GUI 600 is presented and updated in real-time during the procedure.

Figure 9:
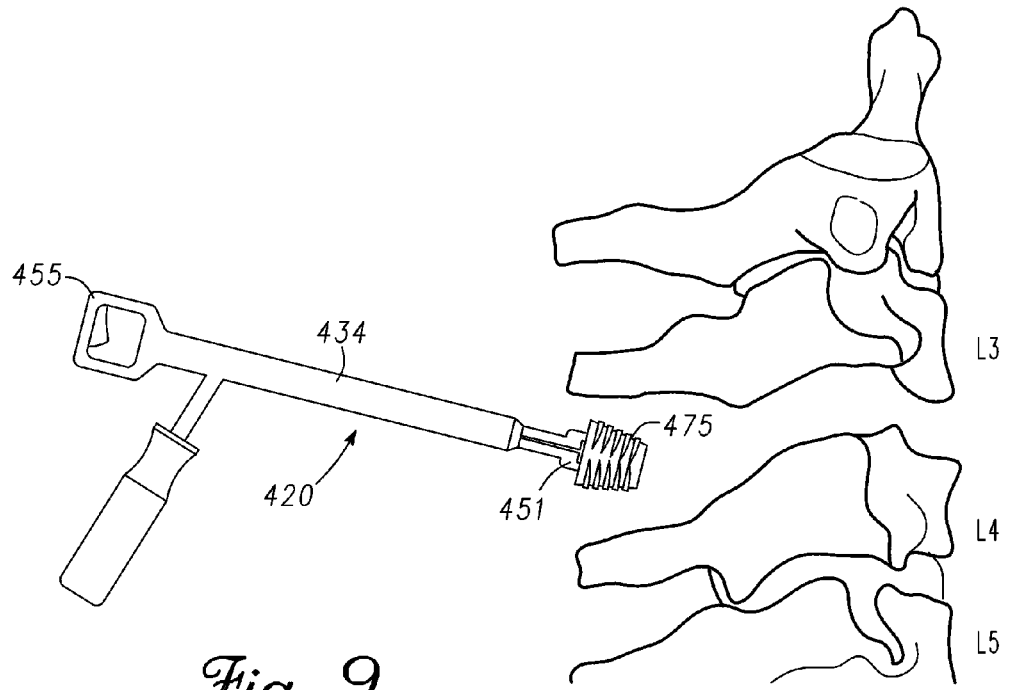
FIG. 9 illustrates a lateral view of the spinal insert instrument for placement of the spine cage in accordance with an example embodiment.

FIG. 9 illustrates a lateral view of spinal insert instrument 420 for placement of spine cage 475 in accordance with an example embodiment. The illustration can also apply to spinal instrument 400 of FIG. 2 and spinal instrument 410 of FIG. 3 when adapted to retain components for insert installation. Insert instrument 420 provides a surgical means for implanting vertebral component 475 (e.g. spine cage, pedicle screw, sensor) between the L3 and L4 vertebrae in the illustration. Mechanical assembly tip 451 at the distal end of shaft 434 permits attaching and releasing of the vertebral component by way of attach/release mechanism 455. The vertebral component 475 can be placed in the back of the spine through a midline incision in the back, for example, via posterior lumbar interbody fusion (PLIF) as shown. The insert instrument 420 can similarly be used in anterior lumbar interbody fusion (ALIF) procedures.

Figure 10:
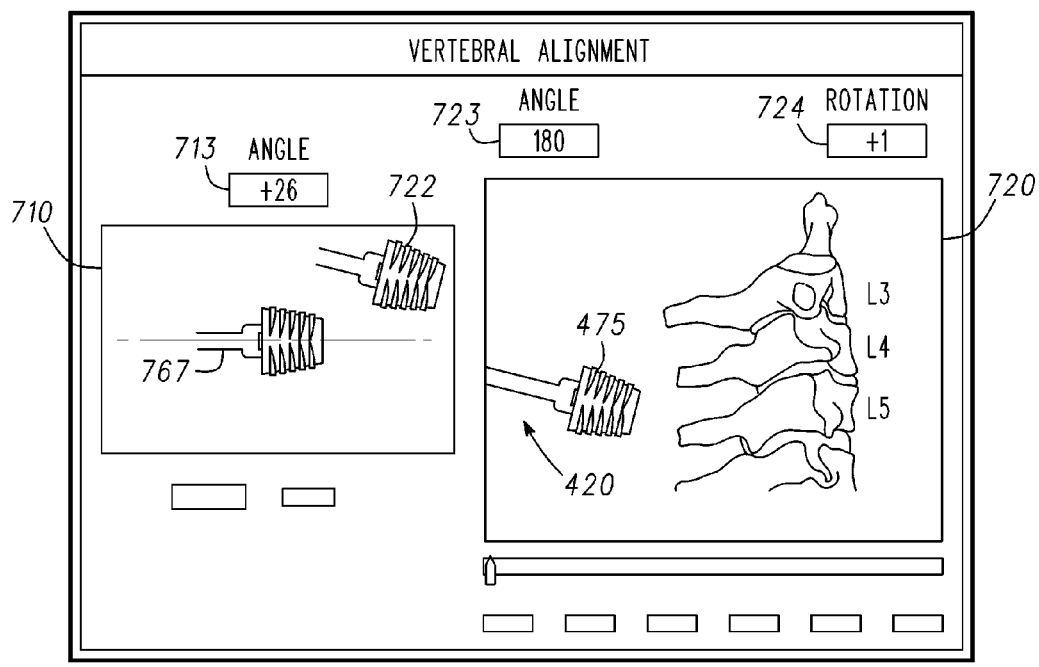
FIG. 10 illustrates the graphical user interface showing the insert instrument of FIG. 9 in a non-limiting example.

In one method herein contemplated, the position of spine cage 475 prior to insertion is optimally defined for example, via 3D imaging or via ultrasonic navigation as described with alignment circuitry 103 of FIG. 1 with spinal instrument 400 shown in FIGS. 6 and 7. The load sensor 407 (see FIG. 7) is positioned between the vertebra to assess loading forces as described above where an optimal insertion path and trajectory is therein defined. The load forces and path of instrument insertion are recorded. Thereafter as shown in FIG. 9, insert instrument 420 inserts the final spinal cage 475 according to the recorded path of spinal instrument 400 and as based on the load forces. During the insertion, the GUI as shown in FIG. 10 navigates the spinal instrument 420 to the recorded insertion point. Spinal insert instrument 420 can be equipped with one or more load sensors serving as a placeholder to a final spinal cage. After placement of spinal cage 475 between the vertebra, release of the spine cage from insert instrument 420, and removal of the insert instrument 420, the open space occupied around the spinal cage is then closed down via rods and pedicle screws on the neighboring vertebra. This compresses the surrounding vertebra onto the spinal cage, and provides stability for vertebral fusion. During this procedure, the GUI 700 of FIG. 10 reports change in spinal anatomy, for example, Lordosis and Kyphosis, due to adjustment of the rods and tightening of the pedicle screws. Notably, the GUI 700 also provides visual feedback indicating which the amount and directions to achieve the planned spinal alignment by way of instrumented adjustments to the rods and screws.

FIG. 10 illustrates graphical user interface (GUI) 700 showing a lateral view of the insert instrument 420 of FIG. 9 in a non-limiting example. GUI 700 can be presented by way of the remote system 105 and measurement system 100 of FIG. 1. GUI 700 includes a window 710 and a related window 720. The window 720 shows insert instrument 420 and vertebral component 475 in relation to the L4 and L5 vertebrae under evaluation. In this example, a sagital (side) view of the spine column is shown. It indicates a shaft angle 723 and a rotation component 724 which reveal the approach angle and rotation of insert instrument 420 and vertebral component 475. Window 720 and corresponding GUI information can be presented and updated in real-time during the procedure. The real-time display permits the surgeon to visualize the vertebral component 475 of the insert instrument 420 according to the previously sensed load force parameters.

Window 710 shows a target sensed head orientation 722 and a current instrument head orientation 767. The target orientation 722 shows the approach angle, rotation and trajectory path previously determined when the spine instrument 400 was used for evaluating loading parameters. The current instrument head orientation 767 shows tracking of the insert instrument 420 currently used to insert the spine cage 475. GUI 700 presents the target orientation model 722 in view of the current instrument head orientation 767 to provide visualization of the previously determined surgical plan.

Referring to FIGS. 1, 5, 6, 7, and 8, spinal instrument 400 is used to assess procedural parameters (e.g., angle, rotation, path) in view of determined sensing parameters (e.g., load, force, edge). Referring back to FIG. 10, once these procedural parameters were determined, measurement system 100 by way of GUI 700 now guides the surgeon with insert instrument 420 to insert the vertebral components 475 (e.g., spine cage, pedicle screw). In one arrangement, measurement system 100 provides haptic feedback to guide insert instrument 420 during the insertion procedure. For example, insert instrument 420 can vibrate when the current approach angle 713 deviates from the target approach angle, provides a visual cue (red/green indication), or when the orientation 767 is not aligned with the target trajectory path 722. The amount of feedback (e.g. haptic or visual) can correspond to the amount of deviation. Alternatively, vocal feedback can be provided by system 100 to supplement the visual and haptic information being provided. The GUI 700 effectively recreates the position and target path of insert instrument 420 through visual and haptic feedback based on the previous instrumenting. It is contemplated herein that spinal instrument 420 can also be adapted for both load measurement and an insertion process.

The loading, balance, and position can be adjusted during surgery within predetermined quantitatively measured ranges through surgical techniques and adjustments using data from sensorized devices disclosed herein for alignment and parameter through measurement system 100. Both the trial and final inserts (e.g., spine cage, pedicle screw, sensors, etc.) can include the sensing module to provide measured data to the remote system for display. A final insert can also be used to monitor the vertebral joint long term. The data can be used by the patient and health care providers to ensure that the vertebral joint or fused vertebrae is functioning properly during rehabilitation and as the patient returns to an active normal lifestyle. Conversely, the patient or health care provider can be notified when the measured parameters are out of specification. This provides early detection of a spine problem that can be resolved with minimal stress to the patient. The data from final insert can be displayed on a screen in real time using data from the embedded sensing module. In one embodiment, a handheld device is used to receive data from final insert. The handheld device can be held in proximity to the spine allowing a strong signal to be obtained for reception of the data.

A method is disclosed for inserting a prosthetic component in a spinal region in a non-limiting example. The method can be practiced with more or less than the number of steps shown and is not limited to the order shown. To describe the method, reference will be made to FIGS. 1, 7, and 9 although it is understood that the method can be implemented in any other manner using other suitable components. In a first step, the spinal region is distracted to create a gap or spacing. The distraction process produces a suitable spacing for receiving a prosthetic component. As disclosed herein, the distraction process can also generate quantitative data such as load and position of load measurements applied by the spinal region to a measurement device of similar size to the prosthetic component. In a second step, the prosthetic component is directed to the spinal region. In the example, an insert instrument is used by a surgeon to direct the prosthetic component held by the tool at a tip of the device. In a third step, the insert instrument measures at least one of orientation, rotation, angle, or position of the prosthetic component. The insert instrument can track a trajectory of the insert instrument and prosthetic component in real-time during the insertion process. In a fourth step, the insert instrument transmits data related to one of orientation, rotation, angle, or position of the prosthetic component and insert instrument. In the example, the data is transmitted wirelessly local to the procedure.

In a fifth step, the transmitted data from the insert instrument is displayed on a remote system. In the example, the remote system can be in the operating room where the procedure is being performed in view of the surgeon. The at least one of orientation, rotation, angle, or position measurement data can be displayed in a manner that allows visualization of the trajectory of the prosthetic component to the spinal region. The visualization allows the surgeon to better direct the prosthetic component where visibility to the region is limited. Furthermore, the visualization provides the benefit of placing the prosthetic component in a previously identified area and at a similar trajectory of the spinal region using quantitative measurement data. In a sixth step, the trajectory of the insert instrument and prosthetic component being tracked can be compared with a trajectory previously measured. The compared trajectories can be displayed and visualized on the display of the remote system.

In a seventh step, the prosthetic component is inserted into the spinal region. In the example, the prosthetic component is placed in the gap or spacing from the prior distraction process. The prosthetic component can be placed in approximately the same location and alignment of a prior device such as the spinal instrument disclosed herein. In an eighth step, the prosthetic component is released in the spinal region. The surgeon can view the placement of the prosthetic component on the remote display. The location and alignment of the prosthetic component is supported by the measurement data provided by the insert instrument. The attach/release mechanism is used to release the prosthetic component from the insert instrument. In a ninth step, the insert instrument is removed from the spinal region. In a tenth step, the insert instrument can be disposed of after the procedure is completed. Alternatively, the insert instrument can be sterilized for use in another procedure.

FIG. 11 is a block diagram of the components of spinal instrument 400 in accordance with an example embodiment. The block diagram can also apply to spinal instrument 410 of FIG. 3 and insert instrument 420 of FIG. 4. It should be noted that spinal instrument 400 could comprise more or less than the number of components shown. Spinal instrument 400 is a self-contained tool that can measure a parameter of the muscular-skeletal system. In the example, the spinal instrument 400 measures load and position of load when inserted in a spinal region. The active components of spinal instrument 400 include one or more sensors 1602, a load plate 1606, a power source 1608, electronic circuitry 1610, a transceiver 1612, and an accelerometer 1614. In a non-limiting example, an applied compressive force is applied to sensors 1602 by the spinal region and measured by the spinal instrument 400.

The sensors 1602 can be positioned, engaged, attached, or affixed to the surfaces 403 and 406 of spinal instrument 400. In general, a compressive force is applied by the spinal region to surfaces 403 and 406 when inserted therein. The surfaces 403 and 406 couple to sensors 1602 such that a compressive force is applied to each sensor. In one embodiment, the position of applied load to surfaces 403 and 406 can be measured. In the example, three load sensors are used in the sensored head to identify position of applied load. Each load sensor is coupled to a predetermined position on the load plate 1606. The load plate 1606 couples to surface 403 to distribute a compressive force applied to the sensored head of spinal instrument 400 to each sensor. The load plate 1606 can be rigid and does not flex when distributing the force, pressure, or load to sensors 1602. The force or load magnitude measured by each sensor can be correlated back to a location of applied load on the surface 403.

In the example of intervertebral measurement, the sensored head having surfaces 403 and 406 can be positioned between the vertebrae of the spine. Surface 403 of the sensored head couples to a first vertebral surface and similarly the surface 406 couples to a second vertebral surface. Accelerometer 1614 or an external alignment system can be used to measure position and orientation of the sensored head as it is directed into the spinal region. The sensors 1602 couple to the electronic circuitry 1610. The electronic circuitry 1610 comprises logic circuitry, input/output circuitry, clock circuitry, D/A, and A/D circuitry. In one embodiment, the electronic circuitry 1610 comprises an application specific integrated circuit that reduces form factor, lowers power, and increases performance. In general, the electronic circuitry 1610 controls a measurement process, receives the measurement signals, converts the measurement signals to a digital form, supports display on an interface, and initiates data transfer of measurement data. Electronic circuitry 1610 measures physical changes in the sensors 1602 to determine parameters of interest, for example a level, distribution and direction of forces acting on the surfaces 403 and 406. The insert sensing device 400 can be powered by an internal power source 1608. Thus, all the components required to measure parameters of the muscular-skeletal system reside in the spinal instrument 400.

As one example, sensors 1602 can comprise an elastic or compressible propagation structure between a first transducer and a second transducer. The transducers can be an ultrasound (or ultrasonic) resonator, and the elastic or compressible propagation structure can be an ultrasound waveguide. The electronic circuitry 1610 is electrically coupled to the transducers to translate changes in the length (or compression or extension) of the compressible propagation structure to parameters of interest, such as force. The system measures a change in the length of the compressible propagation structure (e.g., waveguide) responsive to an applied force and converts this change into electrical signals, which can be transmitted via the transceiver 1612 to convey a level and a direction of the applied force. For example, the compressible propagation structure has known and repeatable characteristics of the applied force versus the length of the waveguide. Precise measurement of the length of the waveguide using ultrasonic signals can be converted to a force using the known characteristics.

Sensors 1602 are not limited to waveguide measurements of force, pressure, or load sensing. In yet other arrangements, sensors 1602 can include piezo-resistive, compressible polymers, capacitive, optical, mems, strain gauge, chemical, temperature, pH, and mechanical sensors for measuring parameters of the muscular-skeletal system. In an alternate embodiment, a piezo-resistive film sensor can be used for sensing load. The piezo-resistive film has a low profile thereby reducing the form factor required for the implementation. The piezo-resistive film changes resistance with applied pressure. A voltage or current can be applied to the piezo-resistive film to monitor changes in resistance. Electronic circuitry 1610 can be coupled to apply the voltage or current. Similarly, electronic circuitry 1610 can be coupled to measure the voltage and current corresponding to a resistance of the piezo-resistive film. The relation of piezo-resistive film resistance to an applied force, pressure, or load is known. Electronic circuitry 1610 can convert the measured voltage or current to a force, pressure, or load applied to the sensored head. Furthermore, electronic circuitry 1610 can convert the measurement to a digital format for display or transfer for real-time use or for being stored. Electronic circuitry 1610 can include converters, inputs, outputs, and input/outputs that allow serial and parallel data transfer whereby measurements and transmission of data can occur simultaneously. In one embodiment, an ASIC is included in electronic circuitry 1610 that incorporates digital control logic to manage control functions and the measurement process of spinal instrument 400 as directed by the user.

The accelerometer 1614 can measure acceleration and static gravitational pull. Accelerometer 1614 can be single-axis and multi-axis accelerometer structures that detect magnitude and direction of the acceleration as a vector quantity. Accelerometer 1614 can also be used to sense orientation, vibration, impact and shock. The electronic circuitry 1610 in conjunction with the accelerometer 1614 and sensors 1602 can measure parameters of interest (e.g., distributions of load, force, pressure, displacement, movement, rotation, torque, location, and acceleration) relative to orientations of spinal instrument 400. In such an arrangement, spatial distributions of the measured parameters relative to a chosen frame of reference can be computed and presented for real-time display.

The transceiver 1612 comprises a transmitter 1622 and an antenna 1620 to permit wireless operation and telemetry functions. In various embodiments, the antenna 1620 can be configured by design as an integrated loop antenna. The integrated loop antenna is configured at various layers and locations on a printed circuit board having other electrical components mounted thereto. For example, electronic circuitry 1610, power source 1608, transceiver 1612, and accelerometer 1614 can be mounted on a circuit board that is located on or in spinal instrument 400. Once initiated the transceiver 1612 can broadcast the parameters of interest in real-time. The telemetry data can be received and decoded with various receivers, or with a custom receiver. The wireless operation can eliminate distortion of, or limitations on, measurements caused by the potential for physical interference by, or limitations imposed by, wiring and cables coupling the sensing module with a power source or with associated data collection, storage, display equipment, and data processing equipment.

The transceiver 1612 receives power from the power source 1608 and can operate at low power over various radio frequencies by way of efficient power management schemes, for example, incorporated within the electronic circuitry 1610 or the application specific integrated circuit. As one example, the transceiver 1612 can transmit data at selected frequencies in a chosen mode of emission by way of the antenna 1620. The selected frequencies can include, but are not limited to, ISM bands recognized in International Telecommunication Union regions 1, 2 and 3. A chosen mode of emission can be, but is not limited to, Gaussian Frequency Shift Keying, (GFSK), Amplitude Shift Keying (ASK), Phase Shift Keying (PSK), Minimum Shift Keying (MSK), Frequency Modulation (FM), Amplitude Modulation (AM), or other versions of frequency or amplitude modulation (e.g., binary, coherent, quadrature, etc.).

The antenna 1620 can be integrated with components of the sensing module to provide the radio frequency transmission. The antenna 1620 and electronic circuitry 1610 are mounted and coupled to form a circuit using wire traces on a printed circuit board. The antenna 1620 can further include a matching network for efficient transfer of the signal. This level of integration of the antenna and electronics enables reductions in the size and cost of wireless equipment. Potential applications may include, but are not limited to any type of short-range handheld, wearable, or other portable communication equipment where compact antennas are commonly used. This includes disposable modules or devices as well as reusable modules or devices and modules or devices for long-term use.

The power source 1608 provides power to electronic components of the spinal instrument 400. In one embodiment, power source 1608 can be charged by wired energy transfer, short-distance wireless energy transfer or a combination thereof. External power sources for providing wireless energy to power source 1608 can include, but are not limited to, a battery or batteries, an alternating current power supply, a radio frequency receiver, an electromagnetic induction coil, a photoelectric cell or cells, a thermocouple or thermocouples, or an ultrasound transducer or transducers. By way of power source 1608, spinal instrument 400 can be operated with a single charge until the internal energy is drained. It can be recharged periodically to enable continuous operation. The power source 1608 can further utilize power management techniques for efficiently supplying and providing energy to the components of spinal instrument 400 to facilitate measurement and wireless operation. Power management circuitry can be incorporated on the ASIC to manage both the ASIC power consumption as well as other components of the system.

The power source 1608 minimizes additional sources of energy radiation required to power the sensing module during measurement operations. In one embodiment, as illustrated, the energy storage 1608 can include a capacitive energy storage device 1624 and an induction coil 1626. The external source of charging power can be coupled wirelessly to the capacitive energy storage device 1624 through the electromagnetic induction coil or coils 1626 by way of inductive charging. The charging operation can be controlled by a power management system designed into, or with, the electronic circuitry 1610. For example, during operation of electronic circuitry 1610, power can be transferred from capacitive energy storage device 1624 by way of efficient step-up and step-down voltage conversion circuitry. This conserves operating power of circuit blocks at a minimum voltage level to support the required level of performance. Alternatively, power source 1608 can comprise one or more batteries that are housed within spinal instrument 400. The batteries can power a single use of the spinal instrument 400 whereby the device is disposed after it has been used in a surgery.

In one configuration, the external power source can further serve to communicate downlink data to the transceiver 1612 during a recharging operation. For instance, downlink control data can be modulated onto the wireless energy source signal and thereafter demodulated from the induction coil 1626 by way of electronic circuitry 1610. This can serve as a more efficient way for receiving downlink data instead of configuring the transceiver 1612 for both uplink and downlink operation. As one example, downlink data can include updated control parameters that the spinal instrument 400 uses when making a measurement, such as external positional information, or for recalibration purposes. It can also be used to download a serial number or other identification data.

The electronic circuitry 1610 manages and controls various operations of the components of the sensing module, such as sensing, power management, telemetry, and acceleration sensing. It can include analog circuits, digital circuits, integrated circuits, discrete components, or any combination thereof. In one arrangement, it can be partitioned among integrated circuits and discrete components to minimize power consumption without compromising performance. Partitioning functions between digital and analog circuit enhances design flexibility and facilitates minimizing power consumption without sacrificing functionality or performance. Accordingly, the electronic circuitry 1610 can comprise one or more integrated circuits or ASICs, for example, specific to a core signal-processing algorithm.

In another arrangement, the electronic circuitry 1610 can comprise a controller such as a programmable processor, a Digital Signal Processor (DSP), a microcontroller, or a microprocessor, with associated storage memory and logic. The controller can utilize computing technologies with associated storage memory such a Flash, ROM, RAM, SRAM, DRAM or other like technologies for controlling operations of the aforementioned components of the sensing module. In one arrangement, the storage memory may store one or more sets of instructions (e.g., software) embodying any one or more of the methodologies or functions described herein. The instructions may also reside, completely or at least partially, within other memory, and/or a processor during execution thereof by another processor or computer system.

The electronics assemblage also supports testability and calibration features that assure the quality, accuracy, and reliability of the completed wireless sensing module or device. A temporary bi-directional coupling can be used to assure a high level of electrical observability and controllability of the electronics. The test interconnect also provides a high level of electrical observability of the sensing subsystem, including the transducers, waveguides, and mechanical spring or elastic assembly. Carriers or fixtures emulate the final enclosure of the completed wireless sensing module or device during manufacturing processing thus enabling capture of accurate calibration data for the calibrated parameters of the finished wireless sensing module or device. These calibration parameters are stored within the on-board memory integrated into the electronics assemblage.

Applications for the electronic assembly comprising the sensors 1602 and electronic circuitry 1610 may include, but are not limited to, disposable modules or devices as well as reusable modules or devices and modules or devices for long-term use. In addition to non-medical applications, examples of a wide range of potential medical applications may include, but are not limited to, implantable devices, modules within implantable devices, intra-operative implants or modules within intra-operative implants or trial inserts, modules within inserted or ingested devices, modules within wearable devices, modules within handheld devices, modules within instruments, appliances, equipment, or accessories of all of these, or disposables within implants, trial inserts, inserted or ingested devices, wearable devices, handheld devices, instruments, appliances, equipment, or accessories to these devices, instruments, appliances, or equipment.

FIG. 12 is a diagram of an exemplary communications system 1700 for short-range telemetry in accordance with an exemplary embodiment. The illustration applies to spinal instrument 400 of FIG. 2, spinal instrument 410 of FIG. 3, insert instrument 420 of FIG. 4, and spine measurement system 100 of FIG. 1. It should be noted that communication system 1700 may comprise more or less than the number of components shown. As illustrated, the communications system 1700 comprises medical device communications components 1710 in a spinal instrument and receiving system communications in a processor based remote system. In one embodiment, the receiving remote system communications are in or coupled to a computer or laptop computer that can be viewed by the surgical team during a procedure. The remote system can be external to the sterile field of the operating room but within viewing range to assess measured quantitative data in real time. The medical device communications components 1710 are operatively coupled to include, but not limited to, the antenna 1712, a matching network 1714, a telemetry transceiver 1716, a CRC circuit 1718, a data packetizer 1722, a data input 1724, a power source 1726, and an application specific integrated circuit (ASIC) 1720. The medical device communications components 1710 may include more or less than the number of components shown and are not limited to those shown or the order of the components.

The receiving station communications components 1750 comprise an antenna 1752, a matching network 1754, a telemetry receiver 1756, the CRC circuit 1758, the data packetizer 1760, and optionally a USB interface 1762. Notably, other interface systems can be directly coupled to the data packetizer 1760 for processing and rendering sensor data.

Referring to FIG. 11, the electronic circuitry 1610 is operatively coupled to one or more sensors 602 of the spinal instrument 400. In one embodiment, the data generated by the one or more sensors 602 can comprise a voltage, current, frequency, or count from a mems structure, piezo-resistive sensor, strain gauge, mechanical sensor, pulsed, continuous wave, or other sensor type that can be converted to the parameter being measured of the muscular-skeletal system. Referring back to FIG. 12, the data packetizer 1722 assembles the sensor data into packets; this includes sensor information received or processed by ASIC 1720. The ASIC 1720 can comprise specific modules for efficiently performing core signal processing functions of the medical device communications components 1710. A benefit of ASIC 1720 is in reducing a form factor of the tool.

The CRC circuit 1718 applies error code detection on the packet data. The cyclic redundancy check is based on an algorithm that computes a checksum for a data stream or packet of any length. These checksums can be used to detect interference or accidental alteration of data during transmission. Cyclic redundancy checks are especially good at detecting errors caused by electrical noise and therefore enable robust protection against improper processing of corrupted data in environments having high levels of electromagnetic activity. The telemetry transmitter 1716 then transmits the CRC encoded data packet through the matching network 1714 by way of the antenna 1712. The matching networks 1714 and 1754 provide an impedance match for achieving optimal communication power efficiency.

The receiving system communications components 1750 receive transmissions sent by spinal instrument communications components 1710. In one embodiment, telemetry transmitter 1716 is operated in conjunction with a dedicated telemetry receiver 1756 that is constrained to receive a data stream broadcast on the specified frequencies in the specified mode of emission. The telemetry receiver 1756 by way of the receiving station antenna 1752 detects incoming transmissions at the specified frequencies. The antenna 1752 can be a directional antenna that is directed to a directional antenna of components 1710. Using at least one directional antenna can reduce data corruption while increasing data security by further limiting the data is radiation pattern. A matching network 1754 couples to antenna 1752 to provide an impedance match that efficiently transfers the signal from antenna 1752 to telemetry receiver 1756. Telemetry receiver 1756 can reduce a carrier frequency in one or more steps and strip off the information or data sent by components 1710. Telemetry receiver 1756 couples to CRC circuit 1758. CRC circuit 1758 verifies the cyclic redundancy checksum for individual packets of data. CRC circuit 1758 is coupled to data packetizer 1760. Data packetizer 1760 processes the individual packets of data. In general, the data that is verified by the CRC circuit 1758 is decoded (e.g., unpacked) and forwarded to an external data processing device, such as an external computer, for subsequent processing, display, or storage or some combination of these.

The telemetry receiver 1756 is designed and constructed to operate on very low power such as, but not limited to, the power available from the powered USB port 1762, or a battery. In another embodiment, the telemetry receiver 1756 is designed for use with a minimum of controllable functions to limit opportunities for inadvertent corruption or malicious tampering with received data. The telemetry receiver 1756 can be designed and constructed to be compact, inexpensive, and easily manufactured with standard manufacturing processes while assuring consistently high levels of quality and reliability.

In one configuration, the communication system 1700 operates in a transmit-only operation with a broadcasting range on the order of a few meters to provide high security and protection against any form of unauthorized or accidental query. The transmission range can be controlled by the transmitted signal strength, antenna selection, or a combination of both. A high repetition rate of transmission can be used in conjunction with the Cyclic Redundancy Check (CRC) bits embedded in the transmitted packets of data during data capture operations thereby enabling the receiving system to discard corrupted data without materially affecting display of data or integrity of visual representation of data, including but not limited to measurements of load, force, pressure, displacement, flexion, attitude, and position within operating or static physical systems.

By limiting the operating range to distances on the order of a few meters the telemetry transmitter 1716 can be operated at very low power in the appropriate emission mode or modes for the chosen operating frequencies without compromising the repetition rate of the transmission of data. This mode of operation also supports operation with compact antennas, such as an integrated loop antenna. The combination of low power and compact antennas enables the construction of, but is not limited to, highly compact telemetry transmitters that can be used for a wide range of non-medical and medical applications.

The transmitter security as well as integrity of the transmitted data is assured by operating the telemetry system within predetermined conditions. The security of the transmitter cannot be compromised because it is operated in a transmit-only mode and there is no pathway to hack into medical device communications components. The integrity of the data is assured with the use of the CRC algorithm and the repetition rate of the measurements. Limiting the broadcast range of the device minimizes the risk of unauthorized reception of data. Even if unauthorized reception of the data packets should occur there are counter measures in place that further mitigate data access. A first measure is that the transmitted data packets contain only binary bits from a counter along with the CRC bits. A second measure is that no data is available or required to interpret the significance of the binary value broadcast at any time. A third measure that can be implemented is that no patient or device identification data is broadcast at any time.

The telemetry transmitter 1716 can also operate in accordance with some FCC regulations. According to section 18.301 of the FCC regulations the ISM bands within the USA include 6.78, 13.56, 27.12, 30.68, 915, 2450, and 5800 MHz as well as 24.125, 61.25, 122.50, and 245 GHz. Globally other ISM bands, including 433 MHz, are defined by the International Telecommunications Union in some geographic locations. The list of prohibited frequency bands defined in 18.303 are "the following safety, search and rescue frequency bands is prohibited: 490-510 kHz, 2170-2194 kHz, 8354-8374 kHz, 121.4-121.6 MHz, 156.7-156.9 MHz, and 242.8-243.2 MHz.

Section 18.305 stipulates the field strength and emission levels ISM equipment must not exceed when operated outside defined ISM bands. In summary, it may be concluded that ISM equipment may be operated worldwide within ISM bands as well as within most other frequency bands above 9 KHz given that the limits on field strengths and emission levels specified in section 18.305 are maintained by design or by active control. As an alternative, commercially available ISM transceivers, including commercially available integrated circuit ISM transceivers, may be designed to fulfill these field strengths and emission level requirements when used properly.

In one configuration, the telemetry transmitter 1716 can also operate in unlicensed ISM bands or in unlicensed operation of low power equipment, wherein the ISM equipment (e.g., telemetry transmitter 1716) may be operated on ANY frequency above 9 kHz except as indicated in Section 18.303 of the FCC code.

Wireless operation eliminates distortion of, or limitations on, measurements caused by the potential for physical interference by, or limitations imposed by, wiring and cables coupling the wireless sensing module or device with a power source or with data collection, storage, or display equipment. Power for the sensing components and electronic circuits is maintained within the wireless sensing module or device on an internal energy storage device. This energy storage device is charged with external power sources including, but not limited to, a battery or batteries, super capacitors, capacitors, an alternating current power supply, a radio frequency receiver, an electromagnetic induction coil, a photoelectric cell or cells, a thermocouple or thermocouples, or an ultrasound transducer or transducers. The wireless sensing module may be operated with a single charge until the internal energy source is drained or the energy source may be recharged periodically to enable continuous operation. The embedded power supply minimizes additional sources of energy radiation required to power the wireless sensing module or device during measurement operations. Telemetry functions are also integrated within the wireless sensing module or device. Once initiated the telemetry transmitter continuously broadcasts measurement data in real time. Telemetry data may be received and decoded with commercial receivers or with a simple, low cost custom receiver.

Figure 13:
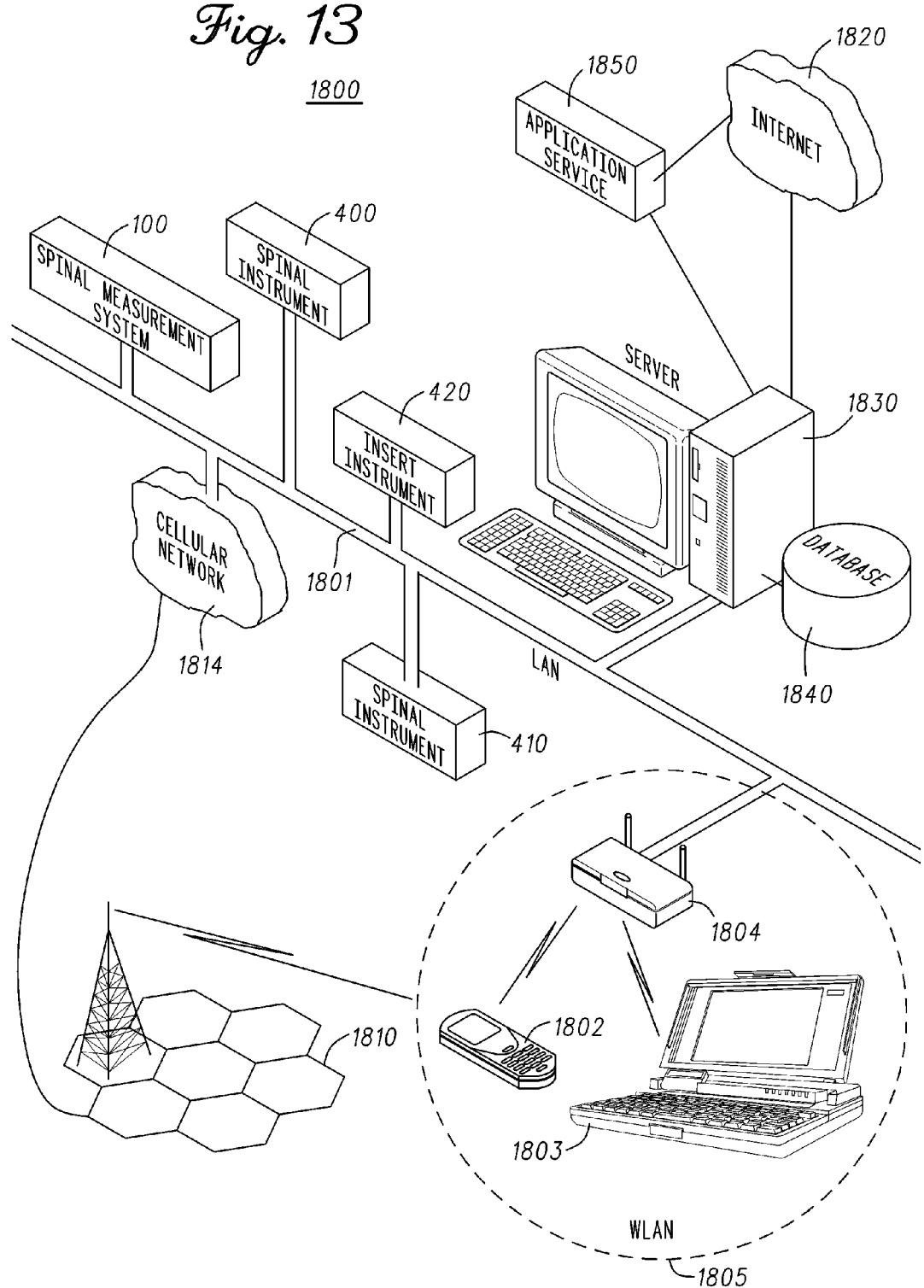
FIG. 13 illustrates a communication network for measurement and reporting in accordance with an example embodiment.

FIG. 13 illustrates a communication network 1800 for measurement and reporting in accordance with an example embodiment. Briefly, the communication network 1800 expands communication for spine measurement system 100 of FIG. 1, spinal instrument 400 of FIG. 2, spinal instrument 410 of FIG. 3, and insert instrument 420 to provide broad data connectivity to other devices or services. As illustrated, spinal alignment system 100, spinal instrument 400, and insert instrument 420 can be communicatively coupled to the communications network 1800 and any associated systems or services. It should be noted that communication network 1800 can comprise more or less than the number of communication networks and systems shown.

As one example, measurement system 100, spinal instrument 400, spinal instrument 410, and insert instrument 420 can share its parameters of interest (e.g., distributions of load, force, pressure, displacement, movement, rotation, torque and acceleration) with remote services or providers, for instance, to analyze or report on surgical status or outcome. In the case that a sensor system is permanently implanted, the data from the sensor can be shared for example with a service provider to monitor progress or with plan administrators for surgical planning purposes or efficacy studies. The communication network 1800 can further be tied to an Electronic Medical Records (EMR) system to implement health information technology practices. In other embodiments, the communication network 1800 can be communicatively coupled to HIS Hospital Information System, HIT Hospital Information Technology and HIM Hospital Information Management, EHR Electronic Health Record, CPOE Computerized Physician Order Entry, and CDSS Computerized Decision Support Systems. This provides the ability of different information technology systems and software applications to communicate, to exchange data accurately, effectively, and consistently, and to use the exchanged data.

The communications network 1800 can provide wired or wireless connectivity over a Local Area Network (LAN) 1801, a Wireless Local Area Network (WLAN) 1805, a Cellular Network 1814, and/or other radio frequency (RF) system. The LAN 1801 and WLAN 1805 can be communicatively coupled to the Internet 1820, for example, through a central office. The central office can house common network switching equipment for distributing telecommunication services. Telecommunication services can include traditional POTS (Plain Old Telephone Service) and broadband services such as cable, HDTV, DSL, VoIP (Voice over Internet Protocol), IPTV (Internet Protocol Television), Internet services, and so on.

The communication network 1800 can utilize common computing and communications technologies to support circuit-switched and/or packet-switched communications. Each of the standards for Internet 1820 and other packet switched network transmission (e.g., TCP/IP, UDP/IP, HTML, HTTP, RTP, MMS, SMS) represent examples of the state of the art. Such standards are periodically superseded by faster or more efficient equivalents having essentially the same functions. Accordingly, replacement standards and protocols having the same functions are considered equivalent.

The cellular network 1814 can support voice and data services over a number of access technologies such as GSM-GPRS, EDGE, CDMA, UMTS, WiMAX, 2G, 3G, WAP, software defined radio (SDR), and other known technologies. The cellular network 1814 can be coupled to base receiver 1810 under a frequency-reuse plan for communicating with mobile devices 1802.

The base receiver 1810, in turn, can connect the mobile device 1802 to the Internet 1820 over a packet switched link. Internet 1820 can support application services and service layers for distributing data from spinal alignment system 100, spinal instrument 400, and insert instrument 420 to the mobile device 502. The mobile device 1802 can also connect to other communication devices through the Internet 1820 using a wireless communication channel.

The mobile device 1802 can also connect to the Internet 1820 over the WLAN 1805. Wireless Local Access Networks (WLANs) provide wireless access within a local geographical area. WLANs are typically composed of a cluster of Access Points (APs) 1804 also known as base stations. Spinal alignment system 100, spinal instrument 400, and insert instrument 420 can communicate with other WLAN stations such as laptop 1803 within the base station area. In typical WLAN implementations, the physical layer uses a variety of technologies such as 802.11b or 802.11g WLAN technologies. The physical layer may use infrared, frequency hopping spread spectrum in the 2.4 GHz Band, direct sequence spread spectrum in the 2.4 GHz Band, or other access technologies, for example, in the 5.8 GHz ISM band or higher ISM bands (e.g., 24 GHz, etc.).

By way of the communication network 1800, spinal alignment system 100, spinal instrument 400, and insert instrument 420 can establish connections with a remote server 1830 on the network and with other mobile devices for exchanging data. The remote server 1830 can have access to a database 1840 that is stored locally or remotely and which can contain application specific data. The remote server 1830 can also host application services directly, or over the internet 1820.

Figure 14:
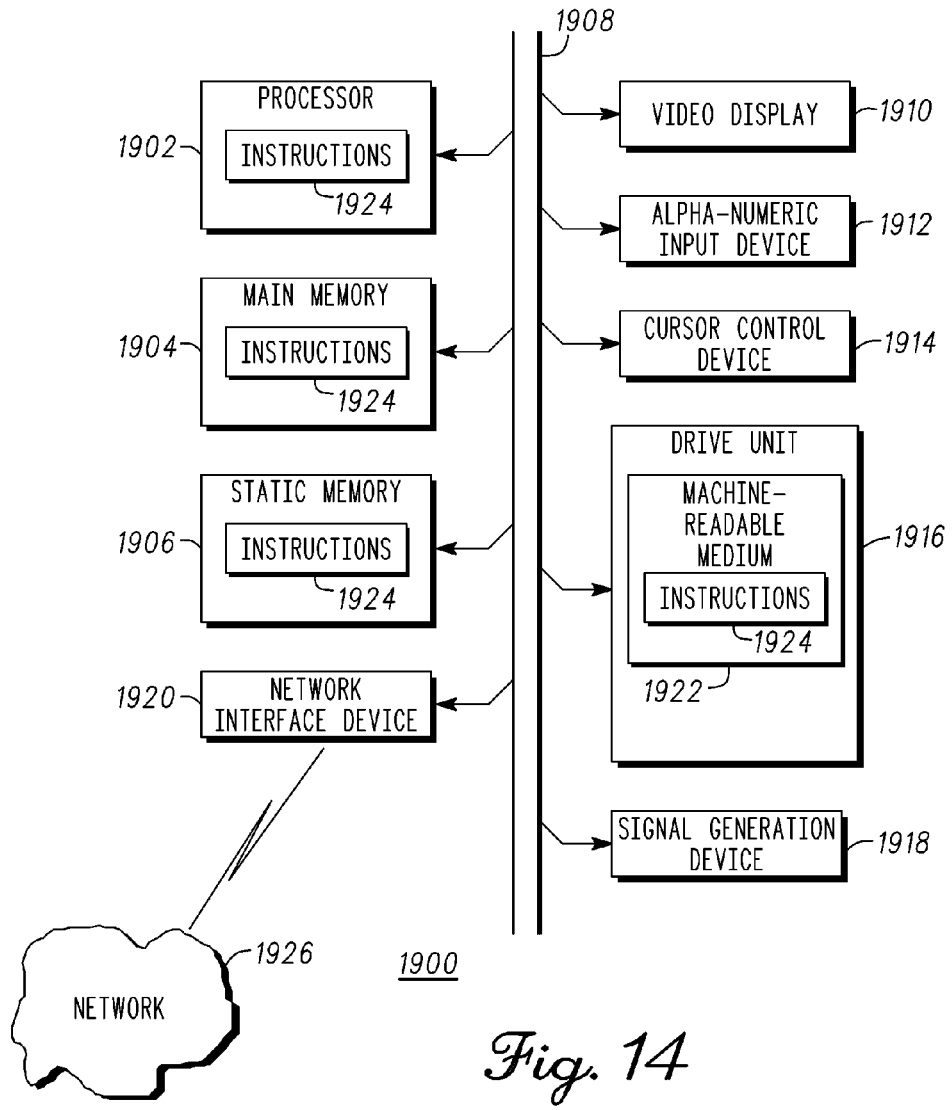
FIG. 14 illustrates an exemplary diagrammatic representation of a machine in the form of a computer system within which a set of instructions, when executed, may cause the machine to perform any one or more of the methodologies disclosed herein.

FIG. 14 depicts an exemplary diagrammatic representation of a machine in the form of a computer system 1900 within which a set of instructions, when executed, may cause the machine to perform any one or more of the methodologies discussed above. In some embodiments, the machine operates as a standalone device. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a laptop computer, a desktop computer, a control system, a network router, switch or bridge, or any machine capable of executing a set of instructions (sequential or otherwise) that specify actions to be taken by that machine. It will be understood that a device of the present disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methodologies discussed herein.

The computer system 1900 may include a processor 1902 (e.g., a central processing unit (CPU), a graphics processing unit (GPU, or both), a main memory 1904 and a static memory 1906, which communicate with each other via a bus 1908. The computer system 1900 may further include a video display unit 1910 (e.g., a liquid crystal display (LCD), a flat panel, a solid-state display, or a cathode ray tube (CRT)). The computer system 1900 may include an input device 1912 (e.g., a keyboard), a cursor control device 1914 (e.g., a mouse), a disk drive unit 1916, a signal generation device 1918 (e.g., a speaker or remote control) and a network interface device 1920.

The disk drive unit 1916 may include a machine-readable medium 1922 on which is stored one or more sets of instructions (e.g., software 1924) embodying any one or more of the methodologies or functions described herein, including those methods illustrated above. The instructions 1924 may also reside, completely or at least partially, within the main memory 1904, the static memory 1906, and/or within the processor 1902 during execution thereof by the computer system 1900. The main memory 1904 and the processor 1902 also may constitute machine-readable media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the present disclosure, the methods described herein are intended for operation as software programs running on a processor, digital signal processor, or logic circuitry. Furthermore, software implementations can include, but not limited to, distributed processing or component/object distributed processing, parallel processing, or virtual machine processing can also be constructed to implement the methods described herein.

The present disclosure contemplates a machine readable medium containing instructions 1924, or that which receives and executes instructions 1924 from a propagated signal so that a device connected to a network environment 1926 can send or receive voice, video or data, and to communicate over the network 1926 using the instructions 1924. The instructions 1924 may further be transmitted or received over a network 1926 via the network interface device 1920.

While the machine-readable medium 1922 is shown in an example embodiment to be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present disclosure.

The term "machine-readable medium" shall accordingly be taken to include, but not be limited to: solid-state memories such as a memory card or other package that houses one or more read-only (non-volatile) memories, random access memories, or other re-writable (volatile) memories; magneto-optical or optical medium such as a disk or tape; and carrier wave signals such as a signal embodying computer instructions in a transmission medium; and/or a digital file attachment to e-mail or other self-contained information archive or set of archives is considered a distribution medium equivalent to a tangible storage medium. Accordingly, the disclosure is considered to include any one or more of a machine-readable medium or a distribution medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are periodically superseded by faster or more efficient equivalents having essentially the same functions. Accordingly, replacement standards and protocols having the same functions are considered equivalents.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

Figure 15:
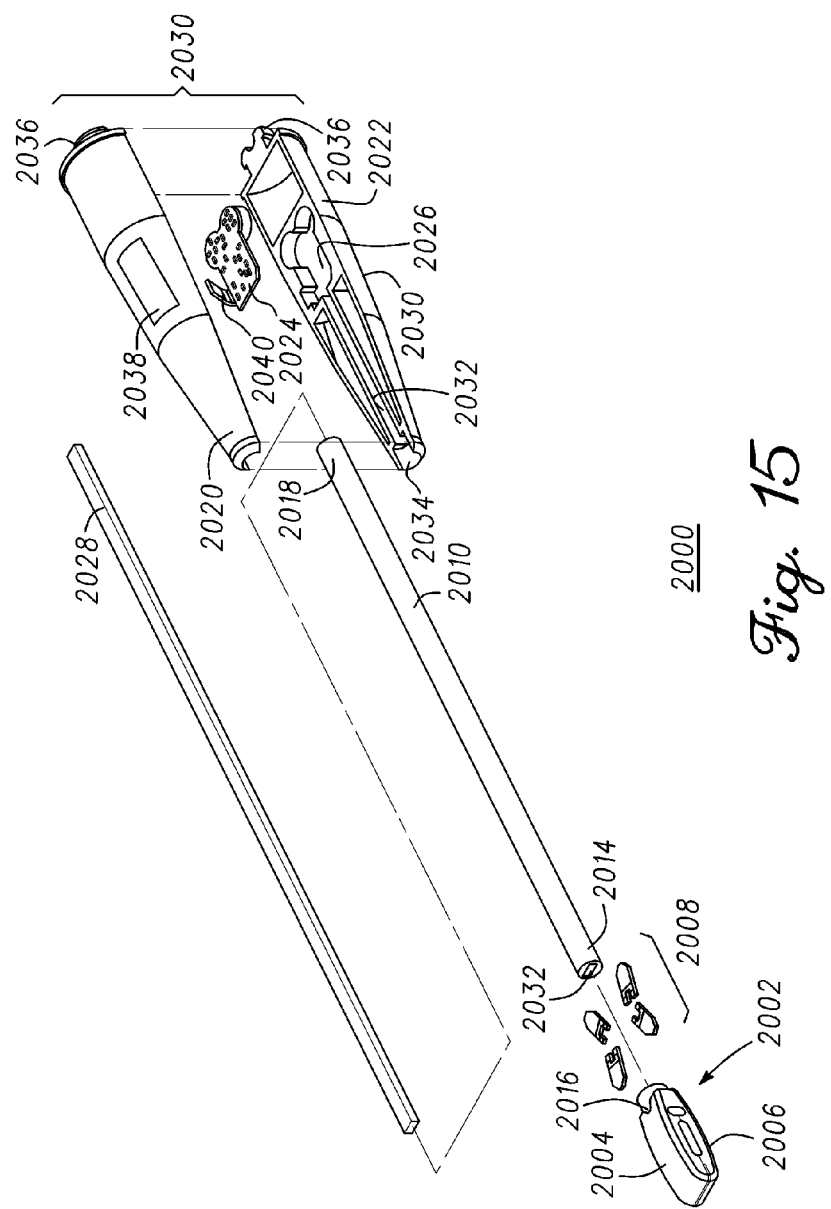
FIG. 15 illustrates components of a spinal instrument in accordance with an example embodiment.

FIG. 15 illustrates components of a spinal instrument 2000 in accordance with an example embodiment. Spinal instrument 2000 is a more detailed illustration of a non-limiting example of spinal instrument 102 of FIG. 1, spinal instrument 400 of FIG. 2, and spinal instrument 410 of FIG. 3. Spinal instrument 2000 is a measurement device having a sensored head 2002 that incorporates at least one sensor for measuring a parameter of the spine. Spinal instrument 2000 comprises sensored head 2002, sensors 2008, shaft 2010, electronic assembly 2024, interconnect 2028, and handle 2030. In one embodiment, handle 2030 is formed by coupling structures 2020 and 2022 together. A proximal end 2018 of shaft 2010 couples to a distal end of handle 2030. A proximal end of sensored head 2002 couples to a distal end 2014 of shaft 2010. Handle 2030 can be held by a surgeon to guide the instrument into the spine region of a patient to take one or more quantitative measurements. Sensored head 2002 can be inserted into the spine region such that the sensors 2008 can measure the parameters of interest. Electronic assembly 2024 operatively couples to sensors 2008 to receive, process, and provide quantitative measurement data. In general, spinal instrument 2000 can provide quantitative measurement data of a probed region by sensors 2008 mounted on or in sensored head 2002. The quantitative data can also support the installation of a component into the muscular-skeletal region. Quantitative data or information related to the procedure can be displayed on an interface 2038 that may be included in spinal instrument 2000. Alternatively, spinal instrument 2000 can provide quantitative data in support of a procedure through a remote system as disclosed herein. The remote system can be wired or wirelessly coupled to spinal instrument 2000. The quantitative data can be provided in real-time with visualization of the procedure.

In the example, sensored head 2002 comprises a support structure 2004 and a support structure 2006. Support structures 2004 and 2006 can move in relation to one another. For example, a compressive force can be applied to external surfaces of support structures 2004 and 2006. Structures 2004 and 2006 can move under the compressive force resulting in a change of height of sensed head 2002. In general, the external surfaces of support structures 2004 and 2006 would move closer together as the applied force or pressure increases. In one embodiment, the movement or change in distance between the external surfaces of support structures 2004 and 2006 is small in relation to the height of sensed head 2002 when no compressive force is applied.

Sensors 2008 are shown disassembled from sensed head 2002. Sensors 2008 are placed within sensed head 2002 when assembled. Sensors 2008 couple between interior surfaces of support structures 2004 and 2006. A compressive force, pressure, or load applied to exterior surfaces of support structures 2004 and 2006 couples to sensors 2008. A measurable parameter of a sensor may directly or indirectly correspond to the force, pressure, or load applied thereto. In one embodiment sensors 2008 are film sensors having a low profile. An example of a film sensor is a piezo-resistive sensor or a polymer sensor. Piezo-resistive film sensors change resistance with an applied force, pressure, or load. Other sensor types can be used as disclosed herein. In general, each sensor is located at a predetermined position within sensed head 2002. The predetermined position can couple to a predetermined location on the external surfaces of support structures 2004 and 2006. Locating each sensor at a known predetermined position supports the determination of the location of applied load to exterior surfaces of support structures 2004 and 2006. As shown, four sensors are placed within sensed head 2002. Typically more than one sensor is used to determine location of applied load. The load measurements of sensors 2008 are assessed in relation with the corresponding location of each sensor. For example, the sensor nearest to the applied load will measure the highest load magnitude. Conversely, the sensor farthest from the applied load will measure the lowest load magnitude. Each sensor measurement can be used in the determination of the location where the load is applied to the exterior surfaces of support structures 2004 and 2006 and the magnitude of the applied load at the identified location.

The resistance of a piezo-resistive film sensor corresponds to the thickness of the film. An applied pressure to piezo-resistive film sensor reduces the thickness thereby lowering the resistance. The surface area of each piezo-resistive sensor is selected to fit within sensed head 2002 and relate to a predetermined location on the external surfaces of support structures 2004 and 2006 for location identification. The surface area of sensors 2008 corresponds to the range of resistance being measured over the measurable load range of spinal instrument 2000. Typically, the magnitude and change in magnitude of the measurable parameter of sensors 2008 over the specified load range is known or measured.

A voltage or current is typically provided by electronic assembly 2024 to piezo-resistive film sensors. For example, providing a known current to the piezo-resistive film sensor generates a voltage that corresponds to the resistance. The voltage can be measured by electronic assembly 2024 and translated to a load measurement. Similarly, a known voltage can be applied to the piezo-resistive film sensor. The current conducted by the piezo-resistive film sensor corresponds to the resistance of the device. The current can be measured by electronic assembly 2024 and translated to the load measurement. Accuracy of the measurement can be improved by calibration of each sensor and providing the calibration data to electronic assembly 2024 for providing correction to the measured data. The calibration can compare sensor measurements to known loads applied to sensed head 2002. Calibration can occur over different operating conditions such as temperature. In one embodiment, sensors 2008 may be calibrated as part of a final test of spinal instrument 2000.

As mentioned previously, sensors 2008 comprise four sensors that support the measurement of the position of loading applied to at least one of the external surfaces of support structures 2004 and 2006. In one embodiment, support structures 2004 and 2006 have convex shaped external surfaces that aid in the insertion of sensed head 2002 into the spinal region such as between vertebrae. The height of sensed head 2002 is a distance between the external surfaces of the support structures 2004 and 2006. Sensored head can be used to distract and generate a gap between vertebrae. For example, the surgeon selects a sensed head of a predetermined height to produce a gap approximately equal to the sensed head height.

Shaft 2010 provides a separation distance between handle 2030 and sensed head 2002. The shaft 2010 allows the surgeon to view and direct sensed head 2002 of spinal instrument 2000 into an exposed area of the spine. A distal end 2014 of the shaft 2010 fits into and fastens to a proximal end 2016 of sensed head 2002. In one embodiment, shaft 2010 is cylindrical in shape and includes at least one lengthwise passage 2012. Proximal end 2016 of sensed head 2002 can include an opening for receiving distal end 2014 of shaft 2010. The shaft 2010 can be secured in the opening of sensed head 2002 by mechanical, adhesive, welding, bonding or other attaching method. In one embodiment, the attaching process permanently affixes sensed head 2002 to shaft 2010. The lengthwise passage 2012 of shaft 2010 may be used to couple a component from handle 2030 to sensed head 2002. For example, an interconnect 2028 can couple through the lengthwise passage 2012. The interconnect 2028 extends out of the lengthwise passage 2012 on both distal end 2014 and proximal end 2018 of shaft 2010. Interconnect 2028 couples sensors 2008 to electronic assembly 2024. Similarly, a second lengthwise passage in shaft 2010 can support a threaded rod that couples to a scissor jack within sensor head 2002 for raising and lowering support structures 2004 and 2006 as disclosed herein. Although a cylindrical shape is disclosed, shaft 2010 can be formed having other shapes. In the example, shaft 2010 is rigid and does not bend or flex when used to insert sensed head 2002 into the spine region. In one embodiment, handle 2030, shaft 2010, support structure 2004, and 2006 are formed of a polymer material such as polycarbonate. Alternatively, spinal instrument can comprise metal components or a combination of polymer and metal to form the structure. The metal components can comprise stainless steel.

Handle 2030 comprises a structure 2020 and a structure 2022. The structures 2020 and 2022 can be formed to include one or more cavities, slots, or openings. A cavity 2026 is shaped to receive electronic assembly 2024 that is housed in handle 2030. The cavity 2026 can include one or more features to support and retain electronic assembly 2024. A slot 2032 can be used to guide and retain interconnect 2028 to electronic assembly 2024 for coupling. Structures 2020 and 2022 couple together to form handle 2030. An opening 2034 on the distal end of handle 2030 receives proximal end 2018 of shaft 2010. In one embodiment, structures 2020 and 2022 can be formed of a polymer or metal. In the example, sensed head 2002, shaft 2010, and structures 2020 and 2022 can be formed by a molding process using a polymer material such as polycarbonate. The structures 2020 and 2022 can be fastened together by mechanical, adhesive, welding, bonding or other attaching method. Similarly, proximal end 2018 of shaft 2010 can be coupled to opening 2034 on the distal end of handle 2030 by mechanical, adhesive, welding, bonding, or other attaching method. In general, the active circuitry within spinal instrument 2000 is isolated from the external environment and a rigid device is formed when sensored head 2002, shaft 2010, and handle 2030 are coupled together. In one embodiment, the sealing process is permanent and spinal instrument 2000 cannot be disassembled to replace components such as the power source (e.g. batteries) that can be included in electronic assembly 2024. The handle 2030 can be formed having a shape that is ergonomic for positioning spinal instrument 2000. The handle 2030 can include weights placed in interior cavities that improve the feel and balance of the device for the surgical procedure. Reinforcement structures can be added to stiffen spinal instrument 2000 thereby reducing device flex. The proximal end of handle 2030 includes a flange 2036 for being tapped by a hammer to aid in the insertion of sensored head 2002 into the spinal region. The flange is sized to accept a standard slap-hammer to aid in the removal of the sensor head from the spinal region. Flange 2036 and the proximal end of handle 2030 are reinforced to withstand hammer taps by the surgeon.

Electronic assembly 2024 controls a measurement process of spinal instrument 2000. In the example, the components of the system are mounted to a printed circuit board. The printed circuit board can have multiple layers of interconnect. Components can be mounted on both sides of the printed circuit board. In one embodiment, the printed circuit board includes a connector 2040 for receiving and retaining interconnect 2028. In the example, interconnect 2028 can be a flexible planar interconnect having copper traces thereon comprising five interconnects for coupling to sensors 2008. A power source such as a battery can be mounted to the printed circuit board for powering electronic assembly 2024. Communication circuitry of electronic assembly 2024 can wirelessly transmit measurement data to a remote system for viewing in real-time. Spinal instrument 2000 can also receive information or data through a wired or wireless connection. Spinal instrument 2000 can include display 2038 with a GUI to locally provide data to the surgeon. Spinal instrument 2000 can also be operatively coupled via a remote sensor system to allow control or feedback through vocal, visual, haptic, gestures, or other communicative means to simplify a workflow or reduce staff required for the procedure.

Figure 16:
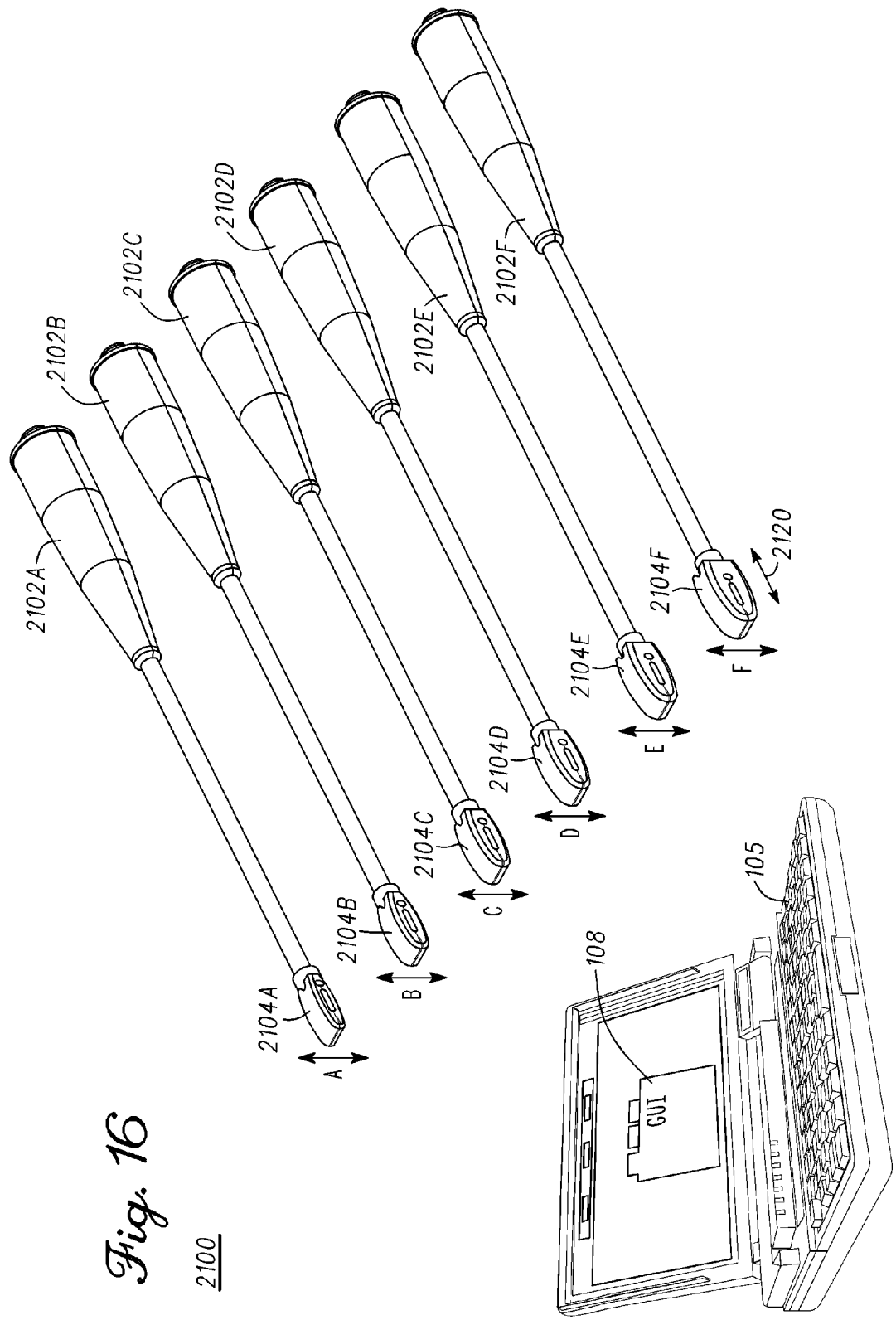
FIG. 16 illustrates a spine measurement system for providing intervertebral load and position of load data in accordance with an example embodiment.

FIG. 16 illustrates a spine measurement system 2100 for providing intervertebral load and position of load data in accordance with an example embodiment. Spine measurement system 2100 is a more detailed illustration of a non-limiting example of spine measurement system 100 of FIG. 1. System 2100 can also include an insert instrument and external alignment devices. The system 2100 comprises spinal instruments 2102A-F (2102A, 2102B, 2102C, 2102D, 2102E, and 2102F) that include active circuitry for measuring a parameter of the muscular-skeletal system. Spinal instruments 2102A-F are a non-limiting example of spinal instrument 400 of FIG. 2, spinal instrument 410 of FIG. 3, and spinal instrument 2000. In the example, spinal instruments 2102A-F each include one or more sensors to measure load and position of load.

The system 2100 comprises a set of spinal instruments 2102A-F where each tool has a different distraction height. Spinal instruments can also be provided having sensored heads of different lengths. As shown, the set of spinal instruments 2102A-F have a sensored head length 2120. An example of sensored heads having different head lengths is disclosed below and can be adapted to system 2100. Each spinal instrument 2102A, 2102B, 2102C, 2102D, 2102E, and 2102F respectively has sensored heads 2104A, 2104B, 2104C, 2104D, 2104E, and 2104F. The surgeon selects the spinal instrument for an appropriate sensored head height that distracts a spinal region appropriate for a patient physiology. As shown, the six sensored heads 2104A, 2104B, 2104C, 2104D, 2104E, and 2104F respectively have heights A, B, C, D, E, and F. The six different heights A-F of sensored heads 2104A-F are an example of what might be provided in a typical system. An example of a distraction height range for a set of sensored heads can be from 6 millimeters to 14 millimeters. An example range of the length of a sensored head can be from 22 millimeters to 36 millimeters. In general, the different height and lengths of sensored heads 2104A-F of system 2100 are chosen to cover a statistically significant portion a patient population a surgeon is likely to see. The actual number of sensored heads having different height and lengths can vary depending on the application. In one embodiment, sensored head height and lengths that are out of the norm can be inventoried in the operating room but may not be part of the set provided initially during the procedure. The inventoried sensored heads can be made available to the surgeon in the event that the set does not provide a suitable sensored head height and length for the patient.

In general, spine measurement system 2100 measures a parameter of the spinal region. In the example, load and position of load are measured. Spinal instruments 2102A-F can also measure the location and position in 3D space with one or more internal accelerometers within each tool. In one embodiment, an accelerometer identifies the trajectory, location and position of the sensored head in real-time. The accelerometer can be located in the handle of spinal instruments 2102A-F with the electronic assembly. The one or more parameter measurements output by system 2100 provide quantitative data to support the procedure. For example, the surgeon exposes the spinal region and views the area of interest. The spinal instruments 2102A-F is made available such that the surgeon can select and use at least one of the tools. Remote system 105 is typically placed outside the sterile field of the operating room. In one embodiment, each spinal instrument 2102A-F may be stored in individual sterilized packaging that is not opened until the surgeon views the spinal region being repaired. The selection of a spinal instrument is patient specific due to variations in spine gap and patient physiology. In the example, the surgeon first determines the appropriate gap height and then opens a sterile package having the spinal instrument with the sensored head of the selected height. In one embodiment, the selected spinal instrument can be placed by a device that can initiate a power up sequence. The enabling process couples an internal power source of the tool to the electronic circuitry and sensors therein. Once powered up, the selected spinal instrument can be coupled to remote system 105. Remote system 105 receives and displays data from the selected spinal instrument. Remote system 105 includes a GUI 107 for controlling user interaction and providing data on a display. The GUI 107 can provide different screens or windows at different steps of the procedure as a workflow that provides quantitative data to the surgeon in one or more formats such that the data supports the surgical outcome.

The surgeon holds the selected spinal instrument by the handle and directs the sensored head between the vertebrae. The enabled spinal instrument sends load, position of load, instrument position, and location data to the remote system 105 where it is displayed in real-time. As mentioned herein, the exterior surfaces of the sensored head are convex in shape such that the tip is narrowed allowing penetration between a separated space between vertebrae prior to distraction. The amount of force required to distract vertebrae can vary. A controlled force applied to the selected spinal instrument may be required to increase the opening between vertebrae. For example, a hammer can be used to tap the flange at the end of the handle of the selected spinal instrument to insert the sensored head between the vertebrae.

In the example, the final position of the sensored head corresponds to the location where a component such as a spinal cage can be placed in a subsequent step. The spinal cage would have a height and length substantially equal to the height and length of the sensored head of the selected spinal instrument. System 2100 measures and displays quantitative data from the selected spinal instrument such as trajectory, position, location, loading, and position of loading of the sensored head. The data supports the placement of the component in the location. More specifically, the loading and position of load on the component placed between the vertebrae can be substantial equal to the quantitative measurements from the selected spinal instrument when the component is placed and located in the final position of the sensored head when distracting the vertebrae.

The surgeon may find that the selected spinal instrument has a sensored head height that is larger or smaller than needed. The surgeon uses as many spinal instruments as required to distract the vertebrae to an appropriate height. This similarly applies to the selection of spinal instruments of different lengths. In one embodiment, the power source within each spinal instruments 2102A-F can power the tool for only a single procedure. Moreover, spinal instruments 2102A-F may not be capable of being sterilized for reuse without compromising the integrity of the device. The spinal instruments that have been removed from sterilized packaging can be disposed of after the surgical procedure is performed. The spinal instruments that remain in sterile packaging can be used in another procedure. The spinal instruments that are disposed of after being used can be replaced to complete the set.

An alternate approach can use a passive set of spinal instruments to do the initial distraction. The passive spinal instruments have no measurement capability. The surgeon identifies an appropriate distraction height between vertebrae with the passive spinal instruments. The set of passive spinal instruments have heads with equal heights as spinal instruments 2102A-F. A spinal instrument is then selected from spinal instruments 2102A-F having a height equal to the identified distraction height made by the passive spinal instrument. The selected spinal instrument is then inserted between the vertebrae. Quantitative data measurements are then taken by the selected spinal instrument in preparation for implanting a component between the vertebrae. The passive spinal instruments can also be low cost disposable or tools that can be sterilized after use. The alternate approach provides the benefit of minimizing the number of spinal instruments 2102A-F used in the procedure.

A method of providing spinal instruments to an operating room is disclosed below. The steps of the method can be performed in any order. The example comprises a system that includes more than one spinal instruments having active circuitry for measurement of a spinal region. The non-limiting example is used to demonstrate a method that is applicable to other muscular-skeletal regions such as the knee, hip, ankle, spine, shoulder, hand, arm, and foot. In a first step, more than one spinal instrument is provided within the operating room. The spinal instruments are in individually sterilized packaging. In one embodiment, the spinal instruments each have a different distraction height and length. The surgeon exposes the spinal region and assesses the patient physiology. In a second step, one of the spinal instruments is selected. In the example, the spinal instrument is selected having an appropriate distraction height for the patient. The spinal instrument is used to measure a parameter of the spinal region such as load and position of load. In a third step, the selected spinal instrument is removed from the sterilized packaging. In a fourth step, the selected spinal instrument is enabled. In the example, the enabling process couples an internal power source to the circuitry in the selected spinal instrument thereby powering up the device for generating quantitative measurement data.

Powering up the selected spinal instrument enables communication circuitry within the device. In a fifth step, the selected spinal instrument couples to a remote system. In the example, the remote system is in the operating room within viewing range of the surgeon. The remote system includes a display for presenting the quantitative measured data from the selected spinal instrument. The remote system can indicate that the selected spinal instrument is enabled by audio, visual, or haptic feedback.

The distraction height can be determined using passive spinal distraction instruments prior to selecting the active spinal instrument. The surgeon selects a passive spinal instrument after the spine region is assessed or exposed. In a sixth step, the spinal region is distracted using the selected passive spinal instrument. The passive spinal instruments have no active circuitry for measurement. In the example, a set of passive spinal instruments has identical heights and lengths as the set of active spinal instruments. In a seventh step, the passive spinal instrument is removed from the spinal region after distraction with the selected passive spinal instrument. In an eighth step, the selected spinal instrument is inserted in the spinal region previously distracted by the selected passive spinal instrument. In the example, the selected spinal instrument has the same height and length as the selected passive spinal instrument. In a ninth step, the selected spinal instrument takes parameter measurements. The data can be wirelessly transmitted to a remote system for display or visualization of the procedure.

One or more of the active spinal instruments can be used during the procedure. In a tenth step, the active spinal instruments that were used to take measurements of the spinal region are disposed of after the procedure. In one embodiment, the passive spinal instruments can go through a sterilization process and are not disposed. Alternatively, the used passive spinal instruments can be disposed similar to the active spinal instruments. In an eleventh step, the spinal instruments that were used and disposed of are replaced. The replacements re-complete the set for a subsequent procedure. The remaining active spinal instruments that were not used are sterile as their sterilized packaging was not opened during the procedure and thus can be reused.

FIG. 17 illustrates a spine measurement system 2200 for providing intervertebral load and position of load data in accordance with an example embodiment. Spine measurement system 2200 is a more detailed illustration of a non-limiting example of spine measurement system 100 of FIG. 1. The system 2200 comprises a remote system 105 and a modular spinal instrument. System 2200 can also include an insert instrument and external alignment devices. The modular spinal instrument comprises a handle 2206, a shaft 2208, a plurality of removable sensored heads 2204A-F, and a module 2210. In general, the spinal instrument is a modular active device having components that can be coupled to handle 2206 and shaft 2208. Three sets of removable sensored heads 2204A-F (2204A, 2204B, 2204C, 2204D, 2204E, and 2204F), 2216A-F (2216A, 2216B, 2216C, 2216D, 2216E, and 2216F), and 2218A-F (2218A, 2218B, 2218C, 2218D, 2218E, and 2218F) are shown in system 2200. There can be more or less than three sets of sensored heads provided in system 2200. Sensored heads 2204A-F, 2216A-F, and 2218A-F can be coupled to or removed from the distal end of shaft 2208. Similarly, module 2210 can be coupled to or removed from a cavity 2214 of handle 2206. An external surface of module 2210 can be shaped as part of an exterior surface of handle 2206 when attached. Module 2210 includes an electrical assembly 2212 comprising electronic circuitry for receiving, processing, and sending quantitative data from sensors in a sensored head. Module 2210 can also include a power source for powering spinal instrument 2202 during a procedure. Electrical interfaces and interconnect couple module 2210 to one of sensored heads 2204A-F when respectively assembled to handle 2206 and shaft 2208.

In general, sensored heads of different heights and different lengths are provided as part of the system for supporting spine measurements over a large statistical population of spine anatomy. The concept can be applied to the configuration disclosed in FIG. 16 where additional sets of spinal instruments can be provided having different sensored head lengths. The modular spinal instrument is a measurement device and a distractor. Removable sensored heads 2204A, 2204B, 2204C, 2204D, 2204E, and 2204F respectively have a sensored head height of A, B, C, D, E, and F. Similarly, removable sensored heads 2216A, 2216B, 2216C, 2216D, 2216E, and 2216F and 2218A, 2218B, 2218C, 2218D, 2218E, and 2218F respectively have head height A, B, C, D, E, and F. The six different heights A-F of sensored heads 2204A-F are an example of what might be provided in a typical system. Each set can set can have more or less than the number of heights show. As mentioned previously, an example range for sensored head heights can be 6 millimeters to 14 millimeters. Sensored heads 2204A-F, 2216 A-F, and 2218A-F respectively have a sensored head length of 2220, 2222, and 2224. The surgeon selects the appropriate sensored head length based on the patient spine anatomy. An example range for sensored head lengths can be from 22 millimeters to 36 millimeters.

The actual number of sensored heads having different heights can vary depending on the application. In one embodiment, sensored head height and length that are out of the norm can be inventoried in the operating room but may not be part of the set provided within the surgical field of the operating room. They can be made available to the surgeon in the event that the set does not provide a suitable sensored head height and length for the patient. The sensored head of spinal instrument 2202 is inserted in the spinal region thereby generating a gap or spacing approximately equal to the height of the sensored head. Spinal instrument 2202A-F is a non-limiting example of spinal instrument 400 of FIG. 2 and spinal instrument 410 of FIG. 3. In the example, spinal instruments 2202A-F includes one or more sensors to measure load and position of load.

In general, system 2200 can be used in an operating room to provide quantitative measurements on the spinal region. A surgeon exposes and reviews the spinal region prior to distraction. The surgeon may select one of the sets of sensored heads 2204A-F, 2216A-F, and 2218A-F respectively having the sensored head lengths 2220, 2222, and 2224. For example, the surgeon chooses the set of sensored heads 2204A-F having the shortest head length 2220. The surgeon can then select one of sensored heads 2204A-F having a height that distracts the spinal region appropriate for a patient physiology. In one embodiment, sensored heads 2204A-F are in individual sterilized packaging. The selected sensored head is removed from the individual sterilized packaging. The surgeon couples the selected sensored head to the distal end of shaft 2208. Similarly, module 2210 is removed from sterilized packaging and installed in handle 2206. System 2200 is then enabled for providing quantitative data from spinal instrument 2202. The enabling process can couple an internal power source of the tool to the electronic circuitry and sensors therein. Once powered up, the selected spinal instrument can be coupled to remote system 105. Remote system 105 will provide indication that spinal instrument 2202 is enabled and operating. Remote system 105 receives and displays data from the selected spinal instrument. Remote system 105 includes a GUI 107 for initiating a workflow, controlling user interaction, and providing data on a display. The GUI 107 can provide different screens or windows at different steps of the procedure as a workflow that provides quantitative data to the surgeon in or more formats such that the data supports the surgical outcome.

The surgeon during the procedure may find that the selected sensored head has a height that is larger or smaller than needed. Spinal instrument 2202 can be removed from the spinal region to replace the sensored head. The sensored head can be replaced as many times as necessary until an appropriate distraction height is achieved and the quantitative measurements of spinal instrument 2202 provide assessment of the spinal region. In one embodiment, the power source within module 2210 can power the tool for a single surgical application. Module 2210 can be sealed to prevent replacement of the power source. Furthermore, after a completed procedure, module 2210 and used sensored heads 2204A-F are disposed of in a manner to prevent reuse. A complete set of sensored heads 2204A-F can be made for a subsequent procedure by replacing the used sensored heads and combining with the unused remaining sensored heads 2204A-F. Spinal instrument 2202 provides the benefit of lowering cost by replacing only a portion of the system.

A method of measuring a spinal region is disclosed below. The steps of the method can be performed in any order. The example comprises a spinal instrument having active circuitry for measuring a parameter, position, and trajectory. The spinal instrument can be used to distract the spinal region. The spinal instrument is modular allowing rapid changes during a procedure to change a distraction height. The non-limiting example is used to demonstrate a method that is applicable to other muscular-skeletal regions such as the knee, hip, ankle, spine, shoulder, hand, arm, and foot.

In a first step, one of a plurality of removable sensored heads is selected. The plurality of sensored heads comprises a set where each sensored head has a different height. One or more sets of sensored heads can be provided where the sensored heads of a set have a different head length than the other sets. In one embodiment, each sensored head is in an individual sterilized package. The selected sensored head is removed from the sterilized packaging. In a second step, a selected sensored head is coupled to a distal end of a shaft of the instrument. In one embodiment, the sensored head and the shaft respectively have a female and male coupling. The male coupling is inserted into the female coupling and locked into place. The locking step can be a rotation of the sensored head to a position that includes one or more retaining features. In a third step, a module is coupled to the spinal instrument. The module includes an electronic assembly for receiving data from sensors in the sensored head. In one embodiment, the module is placed in a cavity of the handle. The module includes a retaining feature that locks it into place in the handle but allows removal of the module. The electronic assembly operatively couples to the sensored head via electrical interfaces and interconnect in the instrument. The instrument can be enabled for taking measurements during the distraction process.

In a fourth step, the sensed head on the instrument is removed. In one embodiment, the active circuitry in the instrument is disabled prior to the sensed head removal process. In the example, the sensed head is rotated back from the locked position such that the shaft can be withdrawn. In a fifth step, a sensed head is selected from the remaining sensed heads. Typically, the previous sensed head is replaced to select a different distraction height based on the patient physiology. As before, the newly selected sensored head is removed from the individualized sterilized packaging. In a sixth step, the newly selected sensored head is coupled to the distal end of the shaft of the instrument as disclosed above. In a seventh step, the instrument is enabled for generating quantitative measurement data on the muscular-skeletal system. The process of enabling couples a power source within the module to the electronic assembly to power the instrument. In one embodiment, the power source is disconnected from the electronic assembly while in the sterilized packaging to prevent discharge and maximize life. In an eighth step, the used sensored heads and the module are disposed of after a procedure. The sensored head and the module are removed from the instrument and disposed of appropriately. In one embodiment, the main body of the instrument comprising the handle and shaft can be sterilized for a subsequent procedure.

FIG. 18 illustrates an exploded view of module 2210 and handle 2206 in accordance with an example embodiment. Module 2210 and handle 2206 are part of spinal instrument 2202 of FIG. 17. Reference can be made to components of FIG. 17 and FIG. 18. A removable module 2210 is a non-limiting example that can be applied to instruments and tools described herein to lower system cost and provide a performance upgrade path. Module 2210 comprises an electronic assembly 2212 for receiving, processing, and sending measurement data from sensors in the sensored head of spinal instrument 2202. Electronic assembly 2212 corresponds to electronic assembly 2024 of FIG. 15 and includes at least some of the circuitry described in FIG. 11 and FIG. 12. Electronic assembly 2212 is sealed within module 2210 and is isolated from an external environment. Module 2210 couples to and is removable from spinal instrument 2202. In general, spinal instrument 2202 includes an electrical interface that couples to module 2210. In the example, spinal instrument 2202 includes a cavity 2214 for receiving module 2210. An electrical interface 2308 in cavity 2214 couples to and aligns with electrical interface 2302 when module 2210 is inserted. In one embodiment, electrical interfaces 2302 and 2308 are held together under pressure to ensure electrical coupling of each interface. For example, electrical interface 2308 can include spring contacts that compress under insertion of module 2210 to maintain coupling under force. A flexible interconnect 2310 couples to electrical interface 2308 in cavity 2214 of handle 2206. Flexible interconnect 2310 extends through the shaft of spinal instrument 2202 for coupling to sensors in a sensored head region of the device.

In the example, module 2210 can be made from a polymer material such as polycarbonate. Module 2210 can be molded in two or more pieces and assemble together to form a housing or enclosure. Electronic assembly 2212 can be placed in a molded cavity that retains and orients the circuitry within module 2210. Electronic assembly 2212 can be coupled to electrical interface 2302 using a flexible interconnect. Electronic assembly 2212 and electrical interface 2302 can include one or more connectors that couple to the flexible interconnect to simplify assembly. The remaining molded pieces can be attached to form the housing or enclosure using sealing methodologies such as adhesives, welding, mechanical fastening, or bonding. In one embodiment, wireless communication is used to send measurement data from spinal instrument 2202 to a remote system for display and visualization. A polymer material such as polycarbonate is transmissive to wireless signals allowing the measurement data to be transmitted from within module 2210 through the enclosure.

Module 2210 further includes a feature 2304 to align and retain the device when coupled to spinal instrument 2202. Feature 2304 fits into opening 2312 when module 2210 is inserting into cavity 2214 of handle 2206. A locking mechanism is shown in an opposing view of module 2210. The locking mechanism comprises a flexible tab 2306 having a flange 2316 that extends from tab 2306. Flange 2316 corresponds and fits into opening 2314 in cavity 2214 of handle 2206. The features 2304 and 2316 respectively in openings 2312 and 2314 retain and prevent module 2210 from disengaging during use of spinal instrument 2202. A removal process of module 2210 requires flexible tab 2306 to be flexed such that flange 2316 is removed from opening 2214. Module 2210 can then be disengaged from cavity 2214 while bending flexible tab 2306 to prevent flange 2316 from coupling to opening 2314.

FIG. 19 illustrates a shaft 2404 for receiving a removable sensored head 2402 in accordance with an example embodiment. The illustration shows a detailed view of sensored head 2402 and a distal end 2404 of shaft 2208 of FIG. 17. Reference can be made to components of FIG. 17 and FIG. 18. Sensored head 2402 corresponds to sensored heads 2204A-F of FIG. 17 for providing an example of a removable sensored head from spinal instrument 2202. In general, a proximal end of sensored head 2402 includes a coupling that mates with a coupling on the distal end 2404 of shaft 2208 of the tool. The couplings mate together to physically attach sensored head 2402 and shaft 2208 for a distraction and measurement process. The coupling on the proximal end of sensored head 2402 and the coupling on distal end 2404 of shaft 2208 when attached form a rigid structure that can be inserted in the spinal region and moved to position the device under load. Sensored head 2402 includes one or more sensors for measuring a parameter of the spinal region. The sensors can be coupled by a flexible interconnect within sensored head 2402 to an electrical interface in proximity to the coupling on sensored head 2402. Similarly, an electronic assembly can be coupled to an electrical interface on the distal end 2404 of shaft 2208 by a flexible interconnect that extends through a lengthwise passage of shaft 2208. The electrical interfaces of sensored head 2402 and distal end 2404 of shaft 2208 align and couple the electrical assembly to the sensors when attached together by the couplings. Thus, sensored head 2402 can be removed and replaced when required during the procedure.

A female coupling is accessible through an opening 2406 at a proximal end of the sensored head 2402 in the example attachment mechanism. A male coupling 2408 extends from distal end 2404 of shaft 2208. The male coupling 2408 comprises a cylindrical extension 2414 having a retaining feature 2416. The coupling types can be reversed such that the male coupling is on sensored head 2402 and the female coupling on distal end 2404 of shaft 2208. An electrical interface 2410 can be formed on the distal end of shaft 2404. Male coupling 2408 extends centrally from electrical interface 2410. Electrical interface 2410 includes spring-loaded pins 2412 for electrical coupling and seals the distal end 2404 of shaft 2208. Spring-loaded pins 2412 are located on a periphery of electrical interface 2410 around male coupling 2408. Spring loaded pins 2412 couple to a flexible interconnect within shaft 2208. Spring loaded pins 2412 can compress under pressure applied by the attaching process. The force applied by spring loaded pins 2412 to the corresponding electrical interface on sensored head 2402 ensures reliable electrical coupling from sensors to the electrical assembly when attached. Spring-loaded pins 2412 include a gasket or seal to isolate an interior of shaft 2208 from an external environment. In one embodiment, electrical interface 2410 can be sealed allowing sterilization of shaft 2404 and handle 2206 for reuse in a subsequent procedure. As shown, there are five spring-loaded pins 2412 on electrical interface 2410. The five pins couple to four sensors in sensored head 2402 and ground. In the example, the four sensors measure load and position of load applied by the spinal region to the exterior surfaces of sensored head 2402.

FIG. 20 illustrates a cross-sectional view of a female coupling 2502 of sensored head 2402 in accordance with an example embodiment. In general, male coupling 2408 couples to female coupling 2602 to retain sensored head 2402 to distal end 2404 of shaft 2208. Reference may be made to FIG. 17, FIG. 18, and FIG. 19. Opening 2406 of sensored head 2402 receives the distal end 2404 of shaft 2208. Female coupling 2502 includes an electrical interface 2504 that corresponds to electrical interface 2410 on distal end 2404 of shaft 2208. Electrical interface 2504 includes electrical contact points 2506 that align to spring loaded pins 2412 when sensored head 2502 is attached to distal end 2404 of shaft 2208. Electrical interconnect 2508 couples electrical contact points 2506 to sensors in sensored head 2402. Female coupling 2502 includes a keyed opening 2510 that is located centrally on the structure. Keyed opening 2510 has a single position that allows retaining feature 2416 to be inserted through female coupling 2502.

In one embodiment, the outer diameter of electrical interface 2410 is approximately equal to or smaller than the inner diameter of opening 2406. The fit of electrical interface 2410 to opening 2406 supports the rigid coupling of sensored head 2402 to shaft 2404. Sensored head 2402 is rotated after retaining feature 2416 is inserted through keyed opening 2510. A spring-loaded barrier 2512 is in a rotation path of retaining feature 2416. Spring-loaded barrier 2512 can compress to approximately surface level of the surface of female coupling 2502. The surface of spring-loaded barrier 2512 can be curved or spherical. Retaining feature 2416 when rotated compresses spring-loaded barrier 2512 and rotates over the structure during the attaching process. The spring in spring loaded barrier 2512 raises the structure back above the surface of female coupling 2502 after retaining feature rotates past. A rotation stop 2514 in the rotation path prevents further rotation of sensored head 2402 by blocking retaining feature 2416.

In one embodiment, retaining feature 2416 is stopped between rotation stop 2514 and spring-loaded barrier 2512. Rotation stop 2514 and spring loaded barrier 2512 form a barrier to prevent movement and rotation of sensored head 2402 when in use. Furthermore, rotation stop 2514 positions sensored head 2402 such that electrical interface 2504 and electrical interface 2410 are aligned for coupling sensors in sensored head 2402 to the electrical assembly for providing sensor measurement data. In general, retaining feature 2416 is held against the surface of female coupling 2502 under force. For example, the rotation path of retaining feature 2416 can be sloped to increase the force between retaining feature 2416 and the surface of female coupling 2502 as it approaches rotation stop 2514. Spring loaded pins 2412 can also apply a force that presses retaining feature 2416 to the surface of female coupling 2502.

Figure 21:
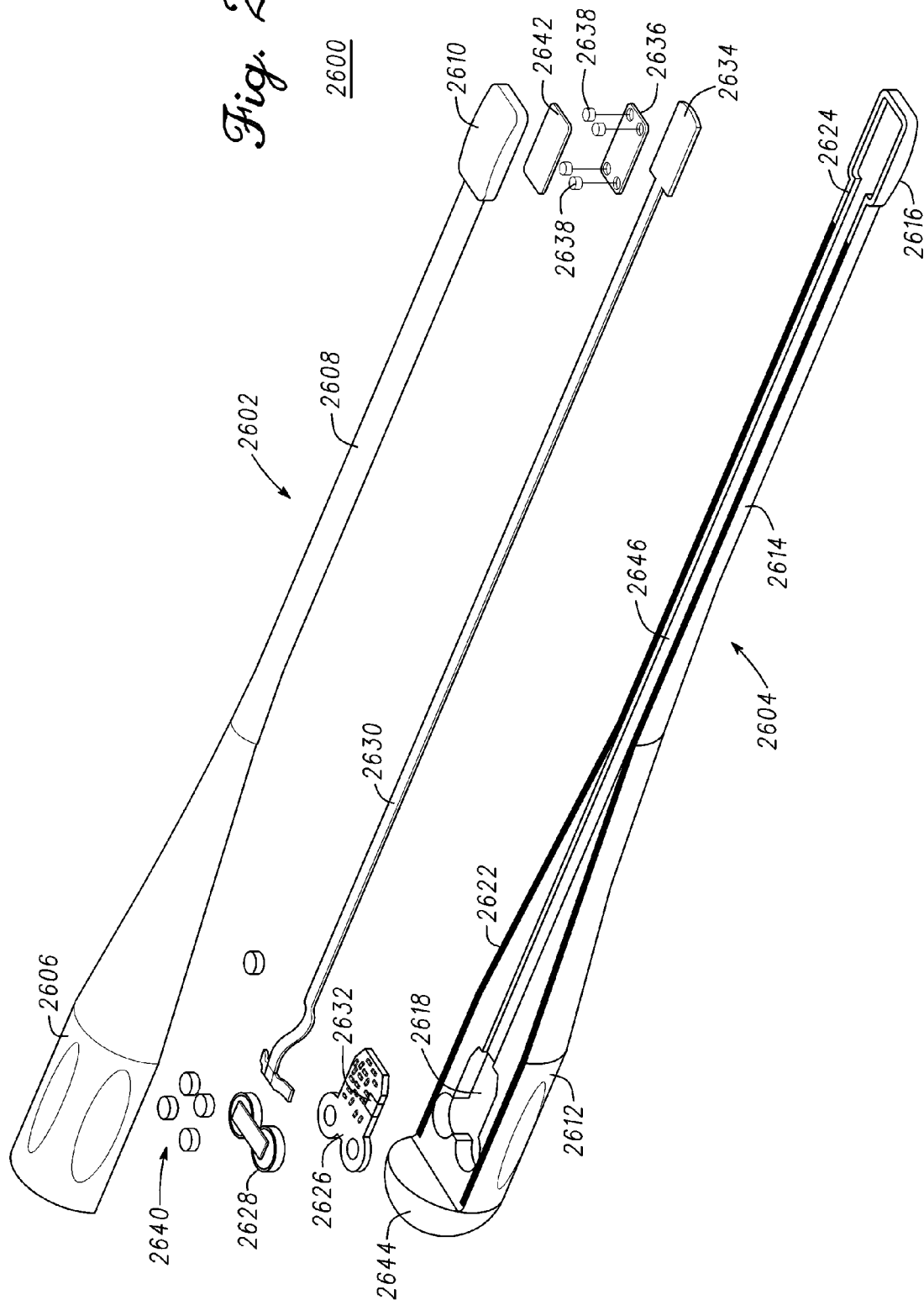
FIG. 21 illustrates an exploded view of a spinal instrument in accordance with an example embodiment.

FIG. 21 illustrates an exploded view of a spinal instrument 2600 in accordance with an example embodiment. Spinal instrument 2600 is a more detailed illustration of a non-limiting example of spinal instrument 102 of FIG. 1, spinal instrument 400 of FIG. 2, and spinal instrument 410 of FIG. 3. Spinal instrument 2600 is a measurement device having a sensored head 2002 that incorporates at least one sensor for measuring a parameter of a spinal region. Spinal instrument 2600 comprises a housing 2602, housing 2604, electronic assembly 2626, interconnect 2630, and sensors 2638. In general, housings 2602 and 2604 couple together to isolate electronic assembly 2626, interconnect 2630, and sensors 2638 from an external environment. Housings 2602 and 2604 respectively include a support structure 2610 and a support structure 2616. Sensors 2638 couple to support structures 2610 and 2616 to measure the parameter of the spinal region. In a surgical procedure, support structures 2610 and 2616 can come in contact with the spinal region. In one embodiment, support structures 2610 and 2616 comprise a sensored head of spinal instrument 2600 that can compress sensors 2638 when a compressive force is applied.

Housing 2602 comprises a handle portion 2606, a shaft portion 2608, and the support structure 2610. Similarly, housing 2604 comprises a handle portion 2612, a shaft portion 2614, and the support structure 2616. Housing 2604 further includes a flange 2644, a cavity 2618, and a lengthwise passage 2646. Flange 2644 is a reinforced structure on a proximal end of the handle of spinal instrument 2600. Flange 2644 can be struck with a hammer or mallet to provide an impact force to insert the sensored head of spinal instrument 2600 into the spinal region. Cavity 2618 supports and retains an electronic assembly 2626. Electronic assembly 2626 receives, processes, and sends quantitative measurements from sensors 2638. A power source 2628 couples to electronic assembly 2626. In one embodiment, the power source can be one or more batteries that are mounted on a printed circuit board of electronic assembly 2626. Electronic assembly 2626 can be coupled to sensors 2638 by a flexible interconnect 2630. Flexible interconnect 2630 can comprise a flexible substrate having patterned electrically conductive metal traces. Electronic assembly 2626 can have one or more connectors that couple to flexible interconnect 2630 to simplify assembly. Flexible interconnect 2630 couples through a lengthwise passage in the shaft of spinal instrument 2600. In one embodiment, lengthwise passage 2646 is used as a channel for flexible interconnect 2630 that couples cavity 2618 to a sensored head region. Retaining features 2640 can retain power source 2628, electronic assembly 2626, and flexible interconnect 2630 in place when assembling spinal instrument 2600. Retaining features 2640 can comprise foam that can be coupled to components and compress without damaging active components as housing 2602 is coupled to housing 2604.

The sensored head of spinal instrument 2600 comprises support structure 2610, support structure 2616, interconnect 2634, sensor guide 2636, and sensors 2638. The exterior surfaces of support structures 2610 and 2616 may be shaped convex to support insertion into the spinal region. Interconnect 2634 is a portion of flexible interconnect 2630 that overlies an interior surface of support structure 2616. Flexible interconnect 2634 includes conductive traces that couple to electrical contact regions of sensors 2638. Sensor guide 2636 overlies interconnect 2634. In one embodiment, interconnect 2634 and sensor guide 2636 can be aligned and retained within support structure 2616 by a peripheral sidewall. Sensor guide 2636 includes openings for retaining and positioning sensors 2638. In the example, sensors 2638 are force, pressure, or load sensors. Interconnect 2634 can have electrical contact regions that align with the openings of sensor guide 2636. The electrical contact regions are exposed for coupling to sensors 2638 through the openings of sensor guide 2636. Sensor guide 2636 also retains and positions sensors 2638 such that the electrical interface of each sensor can couple to a corresponding electrical contact region of interconnect 2634. The electrical interface of sensors 2638 can be coupled to the corresponding electrical contact region of interconnect 2634 by such means as solder, conductive epoxy, eutectic bond, ultrasonic bond, or mechanical coupling. Sensor guide 2636 also positions sensors to couple to support structure 2610 or 2616 at predetermined locations. In one embodiment, sensors 2638 contact an internal surface of support structure 2610 or 2616 that correspond to locations on the external surfaces. Positioning the sensors via sensor guide 2636 allows the position of the applied load on the external surface of support structure 2610 to be calculated. A load plate 2642 can be coupled between sensors 2638 and the interior surface of support structure 2610. Load plate 2642 distributes loading from the interior surface of support structure 2610 to each sensor 2638.

As mentioned previously, housings 2602 and 2604 when coupled together support compression of the sensored head of spinal instrument 2600. A compressive force applied across the external surfaces of support structures 2610 and 2616 is directed to sensors 2638. Other components such as support structure 2610, support structure 2616, load plate 2642, and interconnect 2634 in the compression path do not deform under load. In one embodiment, load plate 2642 comprises a metal such as steel or stainless steel. A compressible adhesive 2624 can be used to couple the periphery of support structures 2610 and 2616 thereby allowing movement of the sensored head and sensors 2638 therein over the measurement range. The compressible adhesive 2624 can be an adhesive such as a silicone based adhesive. The adhesive 2624 is elastic such that the sensored head returns to an unloaded position or moves to a repeatable unloaded height after being compressed. In one embodiment, a second adhesive 2622 is used around a remaining periphery of housings 2602 and 2604 to seal and couple the structures together. Adhesives 2622 and 2624 are applied prior to coupling housings 2602 and 2604 together. Adhesive 2622 can be a bonding adhesive such as a glue or epoxy that mates the peripheral surfaces together. In other words, the bonded surfaces coupled by adhesive 2622 do not have a range of compression as the surfaces are held in contact to one another by adhesive 2622. Alternatively, adhesive 2624 can be used around the entire periphery to couple housings 2602 and 2604 together.

Figure 22:
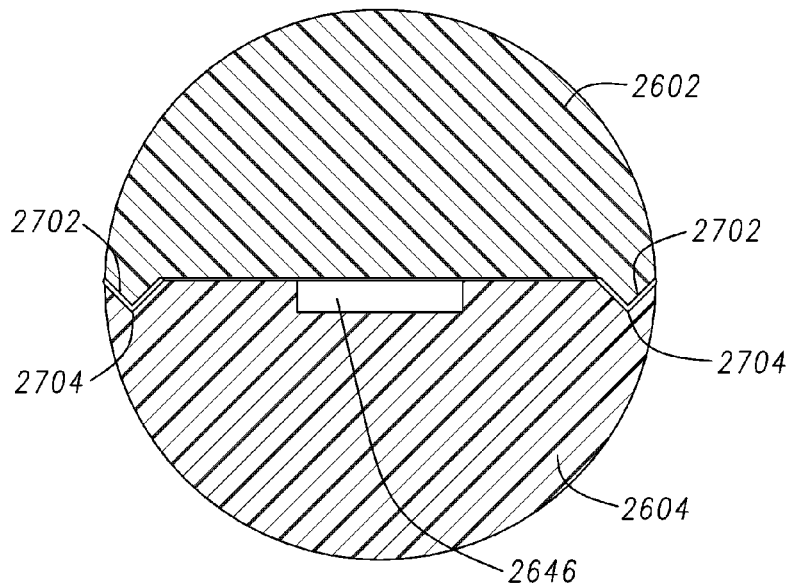
FIG. 22 illustrates a cross-sectional view a shaft region of the spinal instrument of FIG. 21 in accordance with an example embodiment.

FIG. 22 illustrates a cross-sectional view of a shaft region of spinal instrument 2600 in accordance with an example embodiment. The shaft region is a cross-sectional view comprising shaft 2608 and 2614 respectively of housing 2602 and housing 2604 coupled together. The illustration provides detail on the coupling of housings 2602 and 2604 that corresponds a portion of the shaft region and a handle region of spinal instrument 2600. Reference can be made to components of FIG. 21. In general, a housing for the active components of spinal instrument 2600 is formed by coupling housing 2602 to housing 2604. In one embodiment, peripheral surfaces of housing 2602 and housing 2604 are fastened together using more than one adhesive. The peripheral surfaces of housings 2602 and housing 2604 mate such that the structures align, form a barrier, and provide surface area for bonding. In the example, a peripheral surface 2702 of housing 2602 has a geometric shape such as a triangular extension. A peripheral surface 2704 of housing 2604 has a corresponding geometric shape such as a v-shaped groove for receiving the triangular extension. Other tongue and groove geometry can be used such as square, round, or other polygonal shapes. Joints such as a butt-joint or a lap joint can also be used. The profile of the peripheral surfaces of a sensored head region differs from peripheral surfaces 2702 and 2704 of the shaft and handle regions. In the example, surfaces of the triangular extension of peripheral surface 2702 contact surfaces of the v-shaped groove of peripheral surface 2704 when housings 2602 and 2604 are coupled together.

As mentioned previously, peripheral surfaces 2702 and 2704 respectively of housings 2602 and 2604 couple the handle portion and the shaft portion of spinal instrument 2600. Peripheral surface 2702 fits into peripheral surface 2704 providing alignment feedback during assembly. Referring to FIG. 21, the handle portion and the shaft portion corresponds to the area where adhesive 2622 are applied. In the example, adhesive 2622 attaches or bonds peripheral surfaces 2702 and 2704 together with no play or gap between the surfaces other than the adhesive material. In one embodiment, the handle portion and the shaft portion coupled by peripheral surfaces 2702 and 2704 cannot be disassembled without damage to the housing due to the bond integrity of the joint. The shape of peripheral surfaces 2702 and adhesive 2622 seals and isolates an interior of spinal instrument 2600 from an external environment. As shown, a portion of the distal end of the shaft and the peripheral surfaces of support structures 2610 and 2616 can have a different profile as disclosed herein. Similarly, other geometric shaped surfaces or curved surfaces can be used for peripheral surfaces 2702 and 2704.

Figure 23:
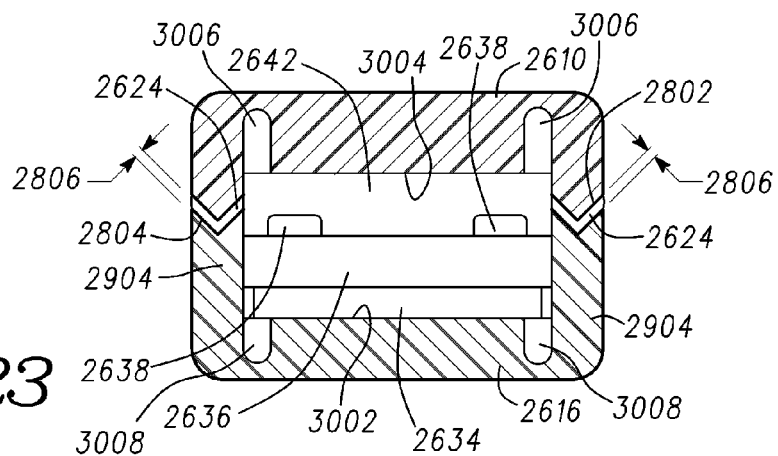
FIG. 23 illustrates a cross-sectional view of a sensored head region of the spinal instrument of FIG. 21 in accordance with an example embodiment.

FIG. 23 illustrates a cross-sectional view of a sensored head region of spinal instrument 2600 in accordance with an example embodiment. The illustration provides detail on the coupling of support structures 2610 and 2616 corresponding to the sensored head region and a distal portion of the shaft region. Reference can be made to components of FIG. 21 and FIG. 22. In general, the sensored head region includes at least one sensor for measuring a parameter of the spinal region. In the example, sensors for measuring a force, pressure, or load are coupled between support structures 2610 and 2616. The support structures 2610 and 2616 compress the sensors when inserted into the spinal region. The sensors output a signal corresponding to the compression. Thus, support structures 2610 and 2616 move in relation to one another allowing compression of the sensors.

As shown, the periphery of housing 2602 and housing 2604 corresponding to support structures 2610 and 2616 of the sensored head region couple together in a manner allowing movement. Support structure 2610 of housing 2602 includes a peripheral surface 2802 having a triangular shaped region. Support structure 2616 of housing 2604 includes a peripheral surface 2804 having a v-shaped groove. In one embodiment, a gap 2806 exists between peripheral surface 2802 and peripheral surface 2804 when housing 2602 is coupled to housing 2604. More specifically, the surfaces of the triangular shaped region of peripheral surface 2802 do not contact the surfaces of the v-shaped groove of peripheral surface 2804 when peripheral surface 2702 of housing 2602 contacts peripheral surface 2704 of housing 2604 as shown in FIG. 22. Gap 2806 allows a compressive force applied to the external surfaces of support structures 2610 and 2616 to move such that the height of the sensored head region is reduced. Gap 2806 is larger than a change in height of the sensors over the measurement range of spinal instrument 2600. Although surfaces are shown as triangular and v-groove shaped in the non-limiting example, surfaces 2802 and 2804 can take other shapes that support gap 2806 and movement of support structures 2610 and 2616.

The sensored head region and the portion of the distal end of the shaft corresponds to the area where adhesive 2624 shown in FIG. 21. In the example, adhesive 2624 elastically attach peripheral surfaces 2802 and 2804 together. Adhesive 2624 fills gap 2806 between the peripheral surfaces 2802 and 2804. Support structures 2610 and 2616 form a housing for the sensor assembly of spinal instrument 2600. Adhesive 2624 can compress when a load is applied across support structures 2610 and 2616. Adhesive 2624 rebounds elastically after compression of the support structures 2610 and 2616 thereby returning the sensored head region back to gap 2806 when unloaded. Filling gap 2806 with adhesive 2624 seals and isolates an interior of the sensored head region and the distal end of the shaft from an external environment. In one embodiment, adhesive 2622 and adhesive 2624 are applied at approximately the same time during the assembly process. Adhesive 2622 is applied to at least one of peripheral surfaces 2702 and 2704 of FIG. 22. Similarly, adhesive 2624 is applied to at least one of peripheral surfaces 2802 and 2804. Housing 2602 and housing 2604 are then coupled together to form the housing for the active system of spinal instrument 2600.

In one embodiment, support structure 2610 and support structure 2616 can be modified to make the exterior load bearing surfaces flexible. A peripheral groove 3006 is formed in the support structure 2610. In general the groove is formed circumferentially such that the external load-bearing surface can flex. A force, pressure, or load is directed to sensors underlying the load bearing surface. The flexible support structure load-bearing surface minimizes load coupling that can cause measurement error. For example, grooves 3006 reduce load coupling from peripheral surface 2802 to 2804. Loading applied to the load-bearing surface of support structure 2610 is coupled through interior surface 3004 to load sensors 2638. Grooves 3006 can bound interior surface 3004. A load plate can be used to distribute loading from internal surface 3004 to sensors 2636. Similarly, a groove 3008 is formed circumferentially in support structure 2616 such that the external load-bearing surface of support structure 2616 can flex. A force, pressure, or load applied to the load-bearing surface of support structure 2616 is directed through interior surface 3002 to sensors 2638. The load coupling through surface 2804 to surface 2802 is minimized by the flexible external load-bearing surface of support structure 2616. Grooves 3008 can bound interior surface 3002.

Figure 24:
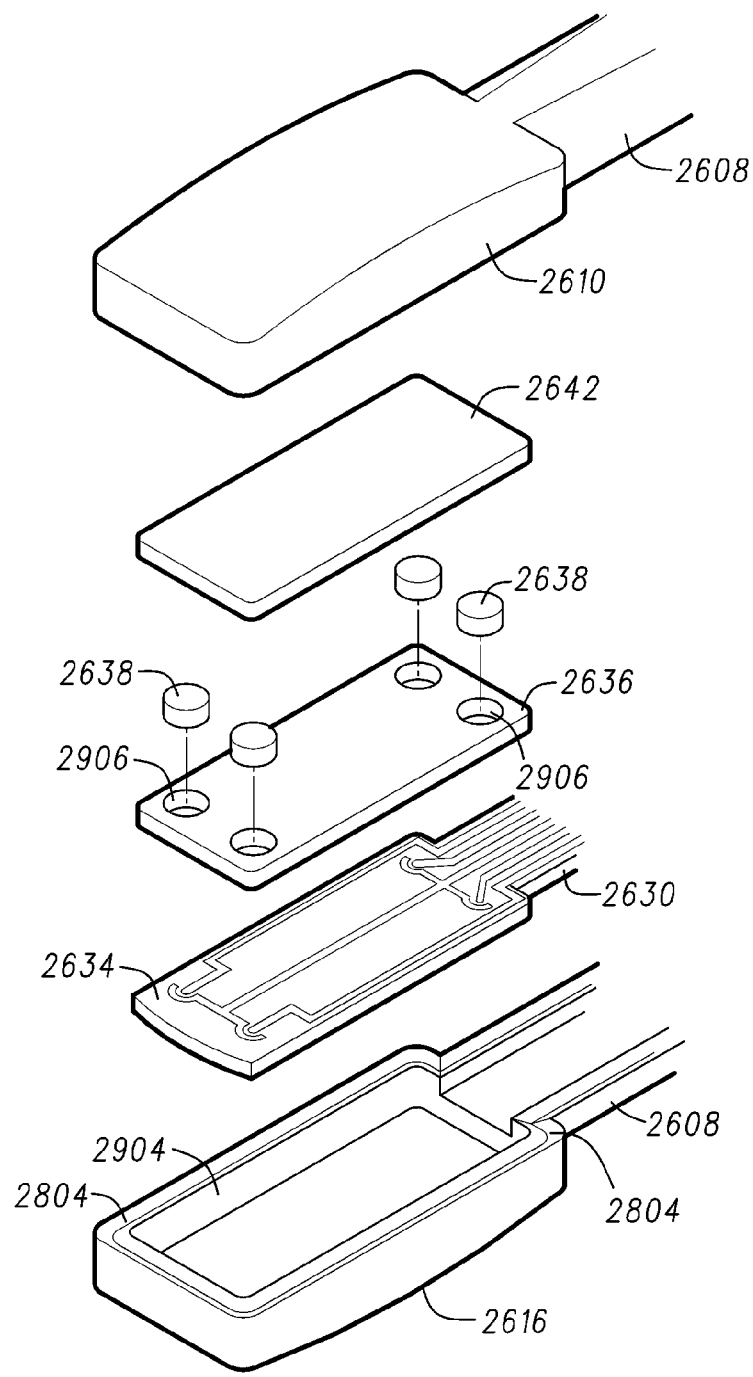
FIG. 24 illustrates an exploded view of the sensored head region of the spinal instrument of FIG. 21.

FIG. 24 illustrates an exploded view of a sensored head region of spinal instrument 2600 in accordance with an example embodiment. In general, support structure 2616 includes a sidewall 2904 having peripheral surface 2804. As shown, the peripheral surface 2804 of sidewall 2904 is a v-groove. Interconnect 2634 of flexible interconnect 2634 couples sensors 2638 to electronic assembly 2626. Flexible interconnect 2634 extends through the shaft of spinal instrument 2600 to the sensored head region. In one embodiment, interconnect 2634 can be shaped to fit in support structure 2616. Interconnect 2634 overlies an interior surface of support structure 2616. Interconnect 2634 is positioned, aligned, and retained on support structure 2616 by sidewalls 2904.

As shown, sensor guide 2636 overlies interconnect 2634. Sensor guide 2636 positions and holds sensors 2838. In one embodiment, sensor guide includes openings 2906 for four sensors. The four sensors 2838 can determine a load magnitude applied to support structures 2610 and 2616 as well as position of the applied load. Electrical contacts of sensor 2638 couple to corresponding contact regions on interconnect 2634. In one embodiment, each sensor 2638 has two contacts, one of which is a common ground. Openings 2906 of sensor guide 2636 align to and expose the underlying interconnect 2634. Moreover, openings 2906 show contact regions of interconnect 2634 for coupling to a sensor. A load plate 2636 can overlie sensors 2638. Load plate 2636 is an optional component for distributing an applied force, load, or pressure applied to support structures 2610 and 2616 to sensors 2638. Load plate 2636 couples to an interior surface of support structure 2610. Load plate 2636 can also be positioned and aligned in the sensored head region by sidewalls 2904 of support structure 2616. Alternatively, support structure 2610 can have a retaining feature for load plate 2636.

Figure 25:
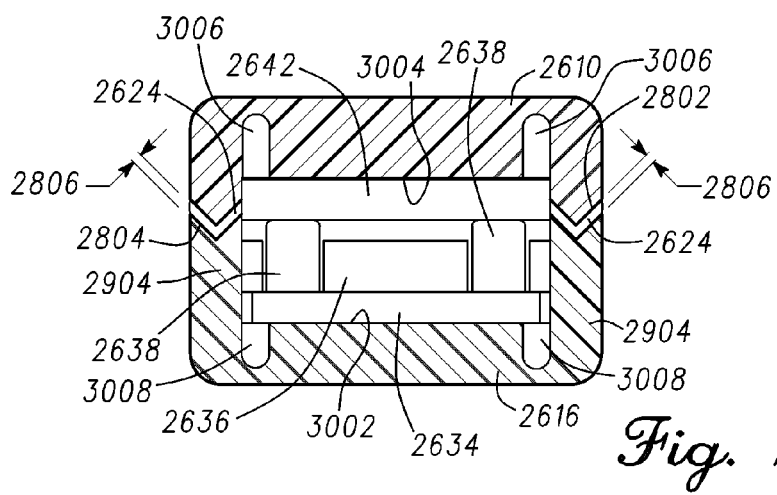
FIG. 25 illustrates a cross-sectional view of the sensored head region of the spinal instrument of FIG. 21 in accordance with an example embodiment.

FIG. 25 illustrates a cross-sectional view of an assembled sensored head region of spinal instrument 2600 in accordance with an example embodiment. The illustration provides detail on the stacked assembly within support structures 2610 and 2616 corresponding to the sensored head region. Reference can be made to components of FIG. 21, FIG. 23, and FIG. 24. Support structure 2616 includes sidewall 2904 that bounds interior surface 3002. In the example, groove 3008 is adjacent to sidewall 2904 and bounds surface 3002 of support structure 2616. Groove 3008 promotes support structure 2616 to flex under loading. Flexible interconnect 2630 couples electronic assembly 2626 to sensors 2638. Flexible interconnect 2630 includes interconnect 2634 that is housed in the sensored head region of spinal instrument 2600. Interconnect 2634 includes contact regions for coupling to sensors 2638. Interconnect 2634 overlies interior surface 3002 of support structure 2616. Interconnect 2634 is retained, aligned, and positioned within the sensored head region by sidewall 3002 of support structure 2616.

Sensor guide 2636 overlies interconnect 2634. Sensor guide 2636 is shaped similar to interconnect 2634. Sensor guide 2636 is retained, aligned, and positioned within the sensored head region by sidewall 2904 of support structure 2616. Sensor guide 2636 has openings that align with the contact regions of interconnect 2634. Sensors 2638 are placed in the openings of sensor guide 2636 such that contacts of sensors 2638 couple to contact regions on interconnect 2634. In one embodiment, sensor guide plate 2636 comprises a non-conductive polymer material. In the example, sensors 2638 extend above a surface of sensor guide 2636 for coupling to load plate 2642 or an interior surface of support structure 2610.

A load plate 2642 is an optional component of the stacked assembly. Load plate 2642 distributes the force, pressure, or load applied to support structures 2610 and 2616 to sensors 2638. In one embodiment, load plate 2642 can be shaped similarly to interconnect 2634 and sensor guide 2634. Load plate 2642 overlies and couples to sensors 2638. In the example, support structure 2610 includes a peripheral sidewall that positions load plate 2642 over sensors 2638. In the example, groove 3006 is adjacent to the peripheral sidewall of support structure 2610 and bounds surface 3004 of support structure 2610. Groove 3006 promotes support structure 2610 to flex under loading. An internal surface 3004 of support structure 2610 couples to load plate 2642. Peripheral surface 2802 of support structure 2610 is coupled to peripheral surface 2804 of support structure 2616 in a manner to support movement under a compressive load. In particular, sensors 2638 can change in height under loading. As disclosed above, elastic adhesive 2624 fills a gap between peripheral surfaces 2802 and 2804. Adhesive 2624 couples support structures 2610 and 2616 together. The adhesive 2624 seals and isolates the stacked assembly of the sensored head region from an external environment. Moreover, adhesive 2624 can compress such that a force, pressure, or load applied to support structures 2610 and 2616 translates from the external surfaces to sensors 2638 for measurement.

While the present invention has been described with reference to particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. An insertion measurement system for the muscular-skeletal system comprising:
    a measurement instrument including:
        a shaft;
        a handle coupled to a proximal end of the shaft;
        a sensored head coupled to a distal end of the shaft configured for insertion into the muscular-skeletal system where the sensored head includes a plurality of load sensors configured to measure load and position of load applied by the muscular-skeletal system onto the sensored head;
        electronic circuitry operatively coupled to the sensored head located in proximity to the handle, and
        a position sensor and alignment circuitry configured to measure at least one of the position, orientation, or trajectory of the sensored head and the measurement instrument during load sensing.

2. The system of claim 1 wherein the sensored head includes four or more load sensors.

3. The system of claim 2 wherein the sensored head comprises:
    a first support structure having an external surface;
    a second support structure having an external surface; and
    a plurality of load sensors coupled to the first and second support structures wherein each load sensor couples to a different predetermined location of the first or second support structure to support position of load measurement.

4. The system of claim 3 wherein the external surfaces of the first and second support structure are convex.

5. The system of claim 3 wherein a load plate underlies the first support structure and overlies the plurality of load sensors and where the load plate is configured to distribute loading to the plurality of sensors to support measurement of load magnitude and position of load.

6. The system of claim 3 further including an interconnect coupling the electronic circuitry to the plurality of load sensors where the interconnect couples through a lengthwise passage in the shaft.

7. The system of claim 6 wherein the electronic circuitry is housed in the handle.

8. The system of claim 1 further comprising:
    an insert instrument including:
        a shaft;
        a tip coupled to a distal end of the shaft;
        an attach/release mechanism coupled to a proximal end of the shaft;
        a handle coupled to the shaft; and
        an electronic assembly wherein the system further includes alignment circuitry configured to measure position, orientation, or trajectory of the insert instrument.

9. The system of claim 8 further including a remote system having a display configured to receive, process, and display data from either the measurement instrument or the insert instrument.

10. A spine measurement system for an operating room comprising:
    a measurement instrument including:
        a shaft;
        a handle coupled to a proximal end of the shaft;
        a plurality of removable sensored heads configured to couple to a distal end of the shaft wherein each removable sensored head includes a plurality of load sensors configured to measure load and position of load applied by the muscular-skeletal system onto the sensored head and wherein each removable sensored head has a different height or length;
        electronic circuitry configured to be operatively coupled to one of the plurality of removable sensored heads where the electronic circuitry is located in proximity to the handle; and
        a position sensor and alignment circuitry configured to measure at least one of the position, orientation, or trajectory of at least one of the sensored heads and the measurement instrument during load sensing; and
    a remote system configured to receive, process, and display data from the measurement instrument.

11. The system of claim 10 wherein the measurement instrument has at least one accelerometer for measuring location and position.

12. The system of claim 10 wherein each removeable sensored head has at least four load sensors.

13. The system of claim 10 further including alignment circuitry configured to measure position, orientation, or trajectory of the measurement instrument and wherein the measurement instrument includes an attach/release mechanism configured to mechanically retain one of the plurality of removable sensored heads and electrically couple one of the plurality of removeable sensored heads to the electronic circuitry.

14. The system of claim 10 further including
    an insert instrument including:
        a shaft;
        a tip coupled to a distal end of the shaft;
        an attach/release mechanism coupled to a proximal end of the shaft;
        a handle coupled to the shaft; and
        an electronic assembly wherein the insert instrument includes alignment circuitry and wherein the alignment circuitry is configured to support guiding the insert instrument to approximately the same position and trajectory as the measurement instrument.

15. The system of claim 10 further including a remote system to receive, process, and display quantitative measurement data.

* * * * *